United States Patent [19]

Klopotek

[11] Patent Number: 5,521,657
[45] Date of Patent: May 28, 1996

[54] METHOD AND SYSTEM FOR TOPOGRAPHIC MEASUREMENT BY MEASURING THE DISTANCE BETWEEN A RIGID REFERENCE MEMBER AND A SURFACE OF AN EYE

[75] Inventor: Peter J. Klopotek, Framingham, Mass.

[73] Assignee: Summit Technology Inc., Waltham, Mass.

[21] Appl. No.: 325,453

[22] PCT Filed: May 3, 1993

[86] PCT No.: PCT/US93/04158

§ 371 Date: Jan. 9, 1995

§ 102(e) Date: Jan. 9, 1995

[87] PCT Pub. No.: WO93/21818

PCT Pub. Date: Nov. 11, 1993

Related U.S. Application Data

[63] Continuation-in-part of Ser. No. 877,651, May 1, 1992, Pat. No. 5,473,392.

[51] Int. Cl.$^6$ .................................................. A61B 3/10
[52] U.S. Cl. ..................... 351/212; 351/221; 351/246
[58] Field of Search ................................. 351/205, 212, 351/219, 221, 246, 247; 606/4, 5, 16

[56] References Cited

U.S. PATENT DOCUMENTS

| | | | |
|---|---|---|---|
| 2,250,521 | 7/1941 | Boeder | 88/20 |
| 4,120,585 | 10/1978 | DePalma et al. | 356/71 |
| 4,309,085 | 1/1982 | Morrison | 351/39 |
| 4,761,071 | 8/1988 | Baron | 351/212 |
| 4,852,987 | 8/1989 | Lohmann | 351/221 |

FOREIGN PATENT DOCUMENTS

| | | | |
|---|---|---|---|
| 1639626 | 4/1991 | U.S.S.R. | 351/212 |
| 8706126 | 10/1987 | WIPO | 606/5 |

OTHER PUBLICATIONS

Warnicki et al., "Corneal topography using computer analyzed rasterstereographic images", Applied Optics, 27:1135, 1988.

Harding, "Current State-of-the-Art of Contouring Techniques in Manufacturing", Journal of Laser Applications, Summer/Fall 1990, pp. 41–47.

Blatt et al., "Video Applications in Moire Metrology", Journal of Laser Applications, Summer/Fall 1990, pp. 35–40.

El Hage, "A Computerized Corneal Topographer for Us in Refractive Surgery", Refractive & Corneal Surgery, 5:418–423, 1989.

Arffa et al., "Corneal Topography Using Rastersterography", Refractive & Corneal Surgery, 5:414–417, 1989.

Lange et al., "Intraoperative Corneal Topographic Measurement Using Phase–Shifted Projected Fringe Contouring", Ophthalmic and Visual Optics, Topical Meeting, pp. 28–31, Jan. 1992.

Wilson et al., "Accuracy and Precision of the Corneal Analysis System and the Topographic Modeling System", Cornea, vol. 11, No. 1, 28–35, 1992.

(List continued on next page.)

Primary Examiner—William L. Sikes
Assistant Examiner—James A. Dudek
Attorney, Agent, or Firm—Fish & Richardson

[57] ABSTRACT

The invention is a system and method of measuring the shape of a surface. The corneal topographer specifically shown comprises a rigid reference member having a reference surface of a predetermined shape applied to the surface of the eye. The shape of the reference surface is correlated with the measured information to determine the shape of the corneal surface. Several specific designs are shown that use optical, acoustic, acousto-optic or capacitive techniques to determine a distance between the reference surface and the corneal surface over a multiplicity of data points sufficient in number and spacing to represent the local topography of the surface of the eye.

41 Claims, 16 Drawing Sheets

OTHER PUBLICATIONS

Wolfendale, "Capacitive displacement transducers with high accuracy and resolution", J. Scientific Instruments (J. Phys. E) 1968 Series 2 vol. 1., pp. 817–818, 1968.

Lin et al., "An Application of White Light Interferometry in Thin Film Measurements", IBM J. Res. Develop., pp. 269–276, May 1972.

Flournoy et al., "White–Light Interferometric Thickness Gauge", Applied Optics, 11:1907–1915, 1972.

Vogel et al., "White Light Interferometry of Elastohydrodynamic Lubrication of Foil Bearings", IBM J. Res. Develop., pp. 521–528, Nov. 1974.

Vienot et al., "Space and time variables in optics and holography: recent experimental aspects", Applied Optics, 16:454–461, 1977.

Caulfield, "White Light Interferometric Microscopes", Optics Communications, 26:322–324, 1978.

Kosel et al., "Capacitive Transducer for Accurate Displacement Control", IEEE Transactions on Instrumentation and Measurement, 1M–30:114–1213, 1981.

Youngquist et al., "Optical coherence–domain reflectometry: a new optical evaluation technique", Optics Letters, 12:158–160, 1987.

Takada et al., "New measurement system for fault location in optical waveguide devices based on an interferometric technique", Applied Optics, 26:1603–1606, 1987.

Williams et al., "Absolute optical ranging with 200–nm resolution", Optics Letters, 14:542–544, 1989.

de la Chapelle et al., "Diode Laser Radar System Analysis and Design for High Precision Ranging", SPIE, 1043:228–237, 1989.

Hee et al., "Polarization–sensitive low–coherence reflectometer for birefringence characterization and ranging", J. Opt. Soc. Am. B, 9:903–908, 1992.

Grattan et al., "Proposed Ranging Technique with Coherent Optical Radiation from Laser Diode Using Phase Shift Method", SPIE 1219:480–489, 1990.

Zharov et al., "Laser Optoacoustic Spectroscopy", Springer–Verlag, pp. 2–4, 9–22, 28–32, 96–102, 1986.

Katri et al., "The Physics of Moire Metrology", John Wiley & Sons, pp. 1–13, 23–27, 89–93, 112–123, 1989.

METHOD AND SYSTEM FOR TOPOGRAPHIC MEASUREMENT BY MEASURING THE DISTANCE BETWEEN A RIGID REFERENCE MEMBER AND A SURFACE OF AN EYE

This application claims priority of PCT application PCT/US93/04158, which is a continuation-in-part of U.S. Ser. No. 07/877,651, filed May 1, 1992, now U.S. Pat. No. 5,473,392.

BACKGROUND OF THE INVENTION

This invention relates to measuring the shape of surfaces. Whereas other uses can be envisioned, the invention has with particular applicability to measurement of the corneal surface and to facilitating treatments of the eye.

Corneal topography measurements are valuable for planning, performing, and evaluating the effects of surgical procedures. Measurements of the corneal surface are needed for keratorefractive procedures, which correct a refractive power of the eye by changing the curvature of the corneal surface. In addition, corneal topography can also be used to predict the results of radial keratotomy, evaluate the design of epikeratophakia for myopia, diagnose the stage of keratoconus, and guide suture removal following corneal transplantation.

There are several methods to test and characterize the optical power of the eye and the cornea in particular. One of the oldest methods is the Snellis diagram test, wherein a patient is asked to read letters or to recognize shapes from a standard distance. This is a subjective method which requires the patient's cooperation.

Since the corneal curvature and its dioptric power account for about three quarters of the refractive power of the eye, it is important, however, to measure the corneal surface with greater accuracy than the Snellis diagram test provides.

One class of methods of measuring the corneal surface is based on the deflectometry principle, which utilizes reflection of light from the smooth corneal tear film (i.e., the lower, oily part of the tear film). In this method, a system of rings is optically projected onto the surface of the eye. A doctor directly observes the symmetry of the reflected rings and judges the condition of the eye. This qualitative technique is quite reliable; however, it is dependent upon the doctor's experience.

In recent years, automatic measurement devices which measure the shiny surface of the cornea using deflectometry have been introduced. These are computerized systems which analyze distortion of the images of a system of rings optically projected towards the eye and detected by a camera detection system. The spatially defined system of rings is projected onto the smooth eye surface from a precisely positioned source governed by a computer. The reflected pattern is detected by a camera and stored in the memory of a computer. Using the well-defined characteristics of the incident and detected light, the geometric position of the source and the detector, and the shapes of the incident and detected pattern the computer calculates the shape of the reflecting sphere.

Such a computerized topographer can be used as a principal guide in a laser system performing corneal sculpturing surgery, to provide the necessary pre-operative and post-operative corneal measurements, or to provide the measurements to guide post-operative manipulation of the cornea for reduction of astigmatism. However, during and after eye surgery, once the epithelium is removed from the eye surface, the local microtopology of the eye surface has changed so that the surface of the eye is only partially a specular reflector, and now partially a diffuse reflector. Since a diffuse reflector has no fixed relationship between the incident angle and the reflected angle of the projected light, the described deflectometry-based topographer is no longer useful. Furthermore, since both the corneal topographer using deflectometry and a laser beam delivery system of a laser sculpturing system require positioning on the optical axis of the eye, there is difficulty in incorporating both systems into one unit designed for intraoperative use. In addition, since the vision of a patient during surgery or after de-epithelization is significantly impaired, it is difficult to achieve proper eye alignment necessary for deflectometric measurement.

Rasterography or fringe phase shifts are methods of determining topography of the cornea which are well suited for diffusive surfaces. The method does not require smooth reflective surfaces and images can be obtained on surfaces with some degree of epithelial irregularity. The methods use an optical pattern, for example, a grid of vertical and horizontal bars of light projected onto the corneal surface. The projected pattern has very well established characteristics including shape, regularity, and separation of the points. A detection system registers and analyzes the deformation of the detected pattern. A computer analyses the deformation data and establishes the topography of the measured surface. The detection system can be located in any place since it detects the light from a diffused reflector which reflects light in all directions. The advantage of this method is that the projected image can cover the entire cornea including the central visual access, far periphery, and limbus, interpalpebral conjunctiva, and lid margins. This technique, however, is not useful for smooth, shiny surfaces, such as the epithelium surface.

There are other optical methods such as confocal microscopy, shared interferometry, infrared interferometry and multi-color interferometry that can be used to characterize the eye surface but each has its limitations and fails to meet fully, for instance, the needs in the case of laser sculpting of the cornea.

Again, as suggested above, in laser sculpting of the cornea, the devices based on deflectometry are well tailored to measure the specular type surface which is the surface of the eye during the initial stages of laser sculpting procedures, and devices based on rasterography are well suited to measure diffuse type corneal surface which occurs after laser sculpturing of the corneal surface was performed, but presently, there are no entirely satisfactory devices which can precisely measure both types of surfaces, and particular surface which in part are of one type and in part another. Neither are there devices which can be conveniently integrated into surgical laser systems. Furthermore, some of the previously mentioned instruments require a patient's cooperation since he or she needs to look in some specific direction.

In general, the discussed topographers are based on the assumption that the cornea has a conic surface i.e. a sphere, an ellipse, a parabola, or a hyperbola, but in reality, the living cornea is none of these; it is an aspheric section with great individual variation, and hence most of the known techniques are not completely accurate.

SUMMARY OF THE INVENTION

According to one aspect of the invention, in laser sculpting of the cornea, the surgeon is informed of the starting profile of the corneal surface and the surface changes during and after the procedure by a single instrument which avoids disadvantages of prior instruments. Advantageous by such a corneal topographer is incorporated into the laser sculpting device itself.

The invention provides a fully automatic corneal topographer which does not rely upon postulation of any corneal surface. Topographers according to the invention are suitable for incorporation into a laser sculpturing system and can reliably measure both specular and diffuse types of surfaces, without requiring significant cooperation of the patient during the measurement procedure.

In one aspect, the invention is a system for determining information concerning the topography of a portion of the exterior surface of the eye. The system includes a rigid reference member having a reference surface of predetermined shape for lying over the portion of the eye; the reference surface being positionable in close proximity to and directed toward the exterior surface of the eye. The system further includes means for determining distance data between the reference surface and the exterior surface of the eye over a multiplicity of data points sufficient in number and spacing to represent the local topography of the surface of the eye, and means for determining the desired information concerning the topography of the surface of the eye from the distance data in reference to the predetermined shape of the reference surface.

Preferred embodiments of this aspect of the invention may include one or more of the following features:

The reference surface of the rigid reference member is concavely shaped to approximate the surface of the eye to enable the space therebetween to have a thin cross-section over the examined portion of the eye, enabling small differences in topography of the eye surface to be detected as relatively large percentage changes in the distance between the reference surface and the eye.

The rigid reference member is transparent to selected radiation and the means for determining the distance data include a detector for detecting the radiation passing through the rigid reference member.

A conformable substance is associated with the rigid reference member. The substance is capable of assuming the conformation of surfaces against which it is engaged and filling the space between the surface of the eye and the reference surface. The means for determining the distance data are adapted to determine thickness data of the conformable substance filling the space between the reference surface and the exterior surface of the eye.

The reference member is transparent to selected radiation and the means for determining the distance between the reference surface and the surface of the eye may be a white light interferometry system, a single color interferometry system or a laser radar system, all adapted to determine the distance data.

The reference member further comprises an array of conductive elements disposed on the reference surface. Each element forms a first capacitor electrode and the corresponding corneal surface forms the other capacitor electrode. The means for determining the distance is a capacitance measurement system adapted to determine the distance data based on the capacitance of the capacitors.

The means for determining the distance data are acoustic means or opto-acoustical means.

The reference member further includes an array of acoustic transducers disposed on the reference surface and adapted to generate and detect acoustic waves across the distance. The means for determining the distance data is an acoustic measurement system adapted to determine the distance data based on the frequency of the acoustic waves.

The reference member is adapted to form with the surface of the eye an acoustic chamber including an acoustic microphone, and the means for determining the distance data is an opto-acoustic measurement system comprise a light source emitting a light beam of a wavelength selected for absorption by a constituent within the chamber, a modulator adapted to modulate the light beam at a frequency selected to excite acoustic waves by absorption of the modulated radiation in the chamber. The acoustic microphone is adapted to detect the acoustic waves across the measured distance which is determined based on the frequency of the acoustic waves.

According to another important aspect of the invention, a system for determining information concerning the topography of a portion of the exterior surface of the eye is provided, the system comprising a rigid reference member having a reference surface of predetermined shape, the reference surface being positionable in close proximity to and directed toward the exterior surface of the eye, a conformable substance capable of assuming the conformation of surfaces against which it is engaged and adapted to fill the space between the surface of the eye and the reference surface of the reference member to conform to the respective surfaces, means for determining thickness data regarding the conformed substance filling the space over a multiplicity of data points sufficient in number and spacing to represent the desired information concerning the topography of the surface of the eye, and means for determining the desired information concerning the topography of the surface of the eye from the thickness data in reference to the predetermined shape of the reference surface.

Preferred embodiments of this aspect of the invention have one or more of the following features.

The reference surface of the rigid reference member is concavely shaped to approximate the surface of the eye to enable the conformable substance to have a thin cross section over the examined portion of the eye, enabling small differences in topography of the eye surface to be detected as relatively large percentage changes in the thickness of the cross-section. The conformable substance comprises a fluid contained by a pliable barrier film supported on the reference member in a manner to confine the fluid, the film having a surface exposed to the eye that is defined by a biologically compatible substance. The reference surface is concave and substantially spherical with a radius of about 8 millimeters. The conformable substance contains a constituent which fluoresces when illuminated by selected radiation such that the intensity of fluorescent emission from points in the substance are dependent upon the thickness of the conformable substance at the points, the system further comprising the reference member being transparent to radiation; a radiation source positioned and adapted to irradiate the conformable substance, when conformed to the surface of the eye and the reference surface, with radiation passing through the reference member; and a detector for detecting the intensity of fluorescent radiation emitted from a multiplicity of points distributed over the conformable substance sufficiently to represent the information concerning the topography of the surface of the eye, the fluorescent radiation returning through the reference member, the intensities being dependent upon the thickness of the fluorescent material at the respective points and constituting the thickness data; preferably in this case the conformable substance comprises a biologically compatible liquid carrying a biologically compatible fluorescent constituent, confined by a biologically compatible barrier film exposed to engage the eye.

As an alternative, the conformable substance comprises a constituent which substantially absorbs radiation passing through the reference member and is contained within a pliable barrier having a surface exposed to the eye formed by a diffusive reflector that produces diffused radiation when illuminated; preferably in this case, the reference member is transparent to selected radiation and the conformable substance substantially absorbs the radiation such that the intensity of diffusively reflected radiation from points in the pliable barrier pressed against the surface of the eye are dependent upon the thickness of the conformable substance at the points, the system further comprising a radiation source positioned and adapted to irradiate the conformable substance, when conformed to the surface of the eye and the reference surface, with incoming radiation passing through the reference member, and a detector for detecting the intensity of diffusely radiation returning from a multiplicity of points distributed over the pliable barrier sufficient to represent the information concerning the topography of the surface of the eye, the intensities dependent upon the thickness of the conformable substance at the respective points and constituting the thickness data.

Any of the systems described above may have one or more of the following features:

The reference member further comprises optical means (e.g., a lens, a Fresnel lens) for substantially directing the returning radiation to the direction of the incoming radiation.

The detector comprises a camera sensitive to radiation received from the reference member. Means are provided for forming an image of detected radiation received via the reference member and determining energy intensities at points in the image. A filter is provided for selecting the wavelength of the radiation detected by the detector. Means are provided to digitize signals of the intensities to obtain the thickness data and computer means for analyzing the data, preferably in which the computer means being adapted to fit the digitized thickness data to a polynomial, the polynomial containing a low order terms representing translational displacements, offset, and angular tilting of the rigid reference member relative to the eye surface, the polynomial also containing higher-order terms representing information about the topography of the eye and the computer means adapted to eliminate the zero order and first order terms.

The detector comprises a lens for receiving radiation through the reference member, a camera upon which the lens focusses an image of the radiation, the camera adapted to produce analog intensity signals, and a frame grabber for producing digital signals from the analog signal for computer analysis.

The system includes means to digitize the thickness data, means to provide a thickness data polynomial by fitting the digitized data to a polynomial, means to provide detailed data of the reference surface, and means to combine the thickness data polynomial with the reference surface topography to provide information about the topography of the eye.

According to another aspect of the invention, a system is provided for determining information concerning the topography of the surface of an object, in general, comprising a rigid reference member having a reference surface directed toward the object, the reference surface being of predetermined shape and the reference member being transparent to radiation, a conformable substance capable of assuming the conformation of surfaces against which it is engaged, the conformable substance comprising a constituent which fluoresces when illuminated by radiation passing through the reference member, such that the intensity of fluorescent emissions from points in the substance are dependent upon the thickness of the substance at the points, means for pressing the rigid reference member relatively against the surface of the object in the manner that the conformable substance conforms, on one side, to the surface of the object, and on the other side to the reference surface of the reference member, a radiation source for irradiating the conformable substance, when conformed to the object and the reference surface with radiation passing through the reference member, a detector for detecting the intensity of fluorescent radiation emitted from a multiplicity of points in the conformable substance sufficient to represent desired information concerning the topography of the surface of the eye, the detector receiving radiation from the conformable substance through the reference member, and means for determining the topography of the surface of the object from the thickness data in reference to the predetermined shape of the reference surface.

According to another aspect of the invention, a system is provided for determining information concerning the topography of the surface of an object, in general, comprising a rigid reference member having a reference surface directed toward the object, the reference surface being of predetermined shape and the reference member being transparent to radiation, a conformable substance capable of assuming the conformation of surfaces against which it is engaged, the conformable substance comprising a constituent which substantially absorbs radiation, the constituent being contained within a pliable barrier having a surface exposed to the surface of the object, the barrier being formed by a diffusive reflector, means for pressing the rigid reference member relatively against the surface of the object in the manner that the conformable substance conforms, on one side, to the surface of the object, and on the other side to the reference surface of the reference member, a radiation source for irradiating the conformable substance, when conformed to the surface of the object and the reference surface with radiation passing through the reference member, a detector for detecting the intensity of diffuse radiation from a multiplicity of points distributed over the pliable barrier sufficient to represent desired information concerning the topography of the surface of the eye, the detector receiving radiation from the multiplicity of points through the reference member, intensities of the detected radiation being dependent upon the thickness of the conformable substance at the respective points and constituting the thickness data, and means for determining the topography of the surface of the object from the thickness data in reference to the predetermined shape of the reference surface.

Other aspects of the invention are methods performing the functions of the systems described above. Other advantages and features of the invention will be apparent from the following description and from the claims.

DESCRIPTION OF THE PREFERRED EMBODIMENTS

Figure 1:
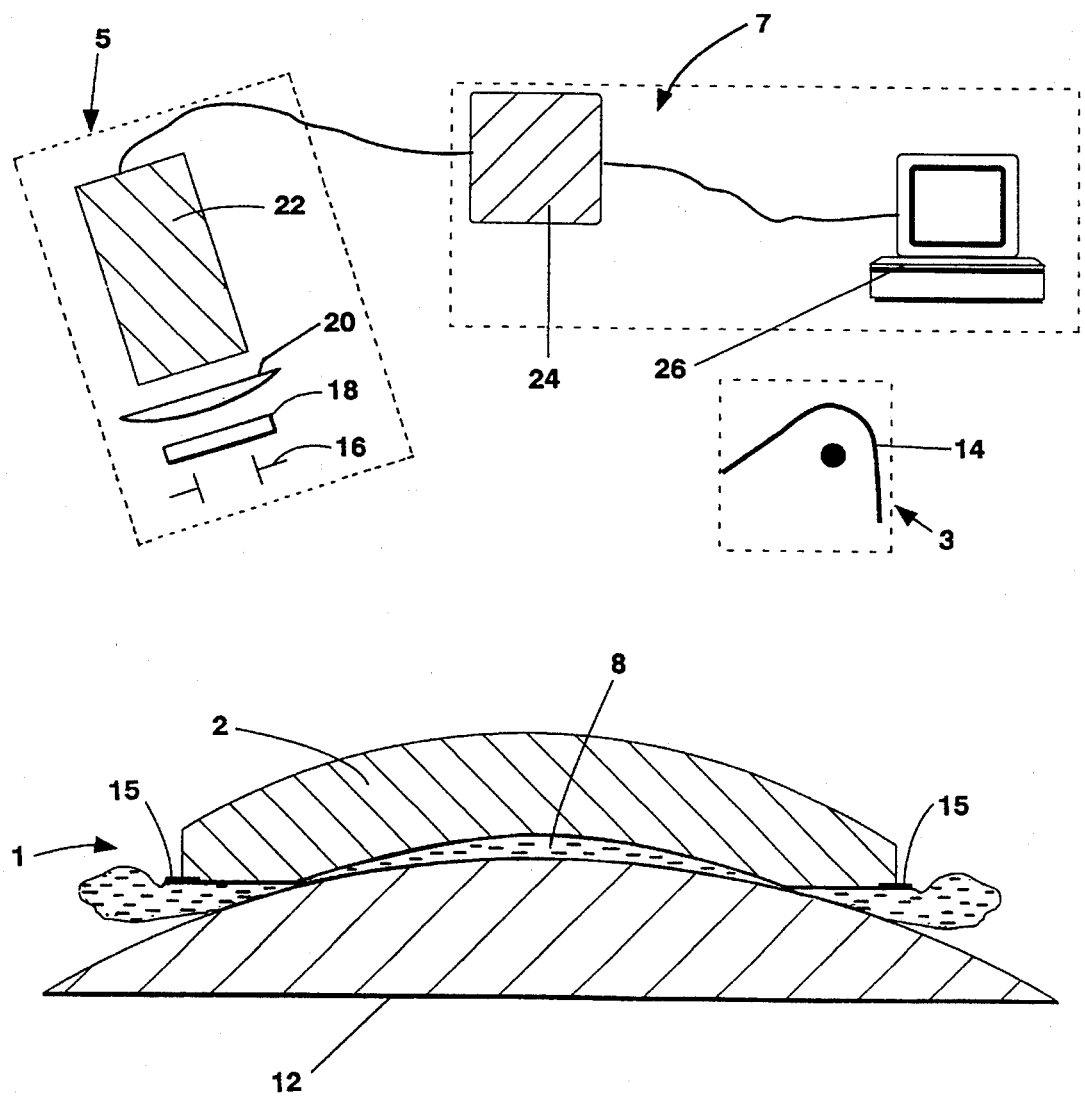
FIG. 1 is a diagrammatic view of a corneal topographer embodying the invention.
Figure 2:
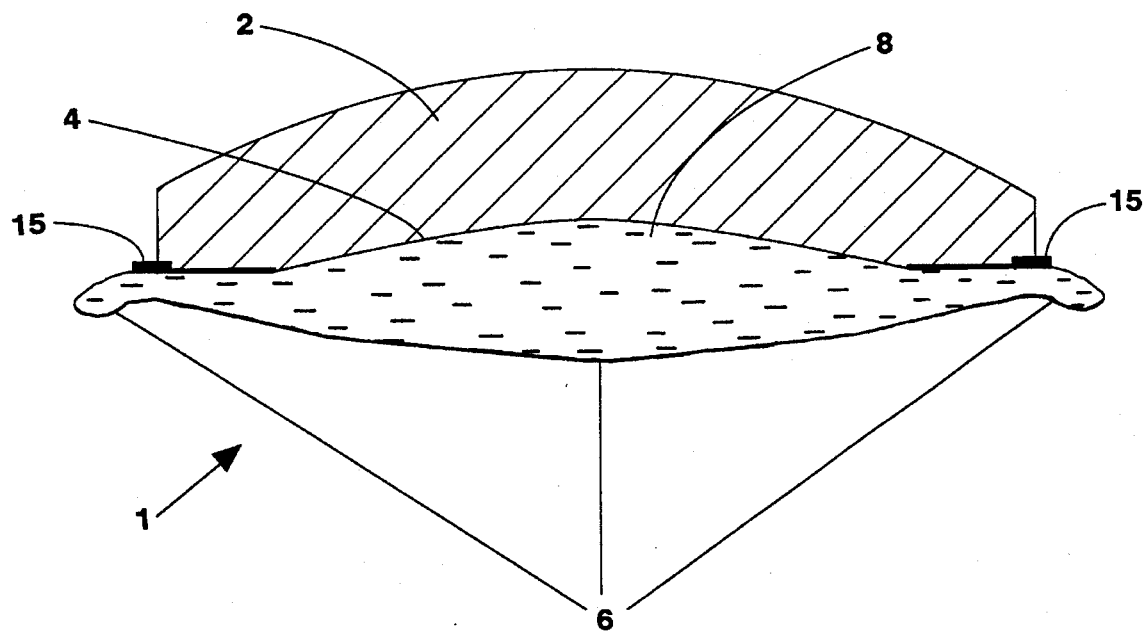
FIG. 2 is a diagrammatic view of a reference eye contact system with a conformable substance.

Referring to FIG. 1, a corneal topographer of the first embodiment comprises a reference eye contact system 1 having a conformable substance, a detection system 5, a light source 3, and a computer system 7. Referring to FIG. 2, eye contact system 1 comprises a rigid reference member 2 made of a transparent material. Reference member 2 has a rigid concavely shaped reference surface 4 of predetermined curvature which conforms to the gross contour expected of eyes. A pliable fluid impermeable conforming membrane 6 is attached to reference member 2 below surface 4 using a fastener ring 15. Membrane 6 confines a dye-containing fluid 8 below reference 4. A fluid reservoir and a small pump, not shown in FIG. 2, can be connected to conforming membrane 6 to vary the amount of fluid present. Conforming membrane 6, while confining the fluid, assumes the shape of a surface it is pressed against.

FIG. 1 shows reference eye contact system 1 pressed against the corneal surface 12. It is expected that the head of a patient will be in a substantially horisontal position during the examination. The pliable membrane 6 and the dye-containing fluid 8 enclosed inside are pressed between rigid reference member 2 and corneal surface 12 so that the space between reference surface 4 and the actual surface of the eye is filled with the dye-containing fluid. The excess fluid and dye are shown present on the sides of rigid reference member 2 within conforming membrane 6. The shape of reference surface 4 approximates the corneal curvature, and thus the amount of the dye-containing fluid located between the two surfaces is very small and of shallow depth. Reference surface 4 is preferably made of a wettable material in order to always fill the space between the two surfaces when eye contact system 1 is applied to the corneal surface 12.

Referring to FIG. 1, detection system 5 contains an adjustable iris 16 for regulating the optical light exposure to a camera 22. The incoming light from reference member 2 is focused by an imaging lens 20 after it is filtered by a wavelength selective filter 18. The filter 18 functions to separate the wavelength of the light of interest from the total incoming light passing through iris 16. The detected signal is processed by a frame grabber and a digitizer 24 connected to camera 22 and is input to a computer 26. Computer 26 is used to analyze and store the digitized signal.

Figure 3:
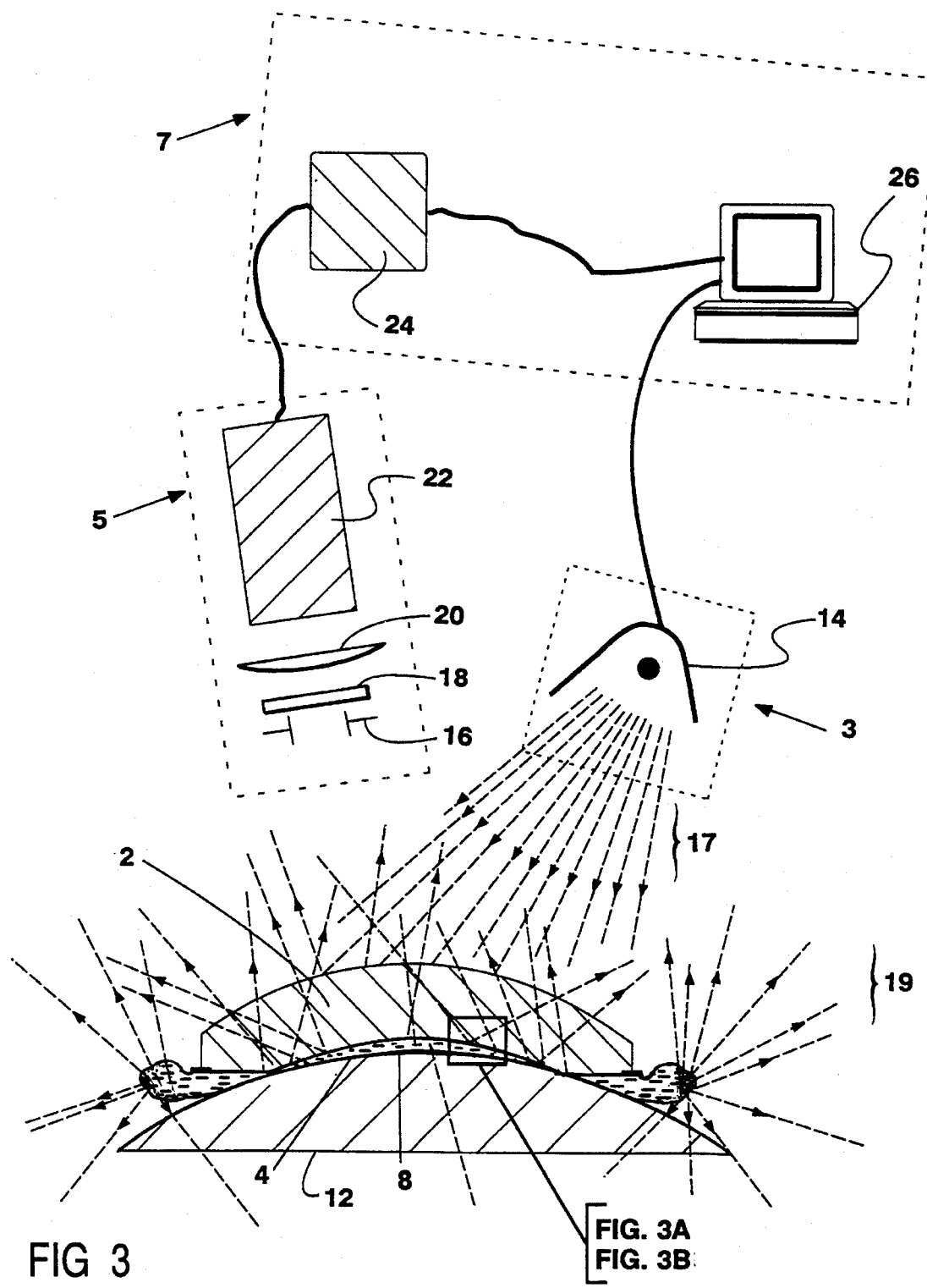
FIG. 3 is a diagrammatic view of the operation of the corneal topographer for first two preferred embodiments of the invention.

The first preferred embodiment utilizing the reference eye contact system of FIG. 2 is a topographer using a differential method of measuring topography by detecting fluorescent radiation. The fluorescent material is a fluorescing constituent which is totally mixed with fluid 8 and confined within conforming membrane 6. Referring to FIG. 3, light source 14 irradiates eye contact system 1, and the incoming radiation passes through transparent rigid reference member 2. The radiation 17 reaches the fluid 8 confined between unknown eye surface 12 and known reference surface 2. The fluorescing fluid is activated by the incident light and emits fluorescent radiation 19. This is diagrammatically shown in FIG. 3A. A portion of the emitted fluorescent radiation passes outwardly through rigid reference member 2 and is detected by detector 22.

As mentioned above, the thickness of the fluorescing fluid filling the space between the two surfaces is very small and varies locally with slight differences between the surfaces. The local thickness of this fluid contains information about the corneal surface. The intensity of the fluorescent light radiated by the fluorescent dye depends, at any point on the thickness of the fluorescent dye contained between the two surfaces. Referring to FIG. 3, detecting system 5 detects fluorescent radiation focused by imaging lens 20 onto camera 22. Filter 18 permits passage only of the fluorescent light and blocks other incoming light entering through iris 16. The detected signal is then digitized by digitizer 24 and stored in the memory of computer 26. The whole measurement process is controlled by the computer 26, which also stores the known source-detector geometry, the shape of reference surface 4, properties of the incident light 17 and of the emitted light 19.

The second preferred embodiment utilizing the reference eye contact system of FIG. 2 is a topographer of similar construction using a differential method of measuring topography by detecting localized absorption of light. The absorbing material is an absorbing constituent which is totally mixed with fluid 8. The absorbing fluid is again confined by pliable conforming membrane 6. In this embodiment, the section of the conforming membrane exposed to the corneal surface 12 comprises a diffusive optical scatterer (for example, Teflon®) and the other sections are made of non-reflecting material. In the measurement process, referring to FIG. 3, eye contact system 1 is pressed against corneal surface 12. Light source 14 irradiates eye contact system 1. The incoming light passes through transparent rigid reference member 2, the absorbing fluid, and that incoming light 17 which is not absorbed by the fluid reaches the diffuser section of the conforming membrane 6. As shown in FIG. 3b, a fraction of light is diffusely reflected and travels back through the absorbing fluid, thence through transparent reference member 2 and is detected by detection system 5. The geometry of source 14, the known shape of reference surface 4, eye contact system 1, and detection system 5 are stored in the memory of computer 26. The light detected by detection system 5 passes twice through the thickness of absorbing fluid confined between known reference surface 4 and the unknown corneal surface 12. The local attenuation of reflected light 19 depends, here again on the local thickness of the absorbing fluid, and thus the local intensity of the detected light possesses the desired information about the thickness of the absorbing fluid of each respective point over the surface of the cornea. In addition to its reference function, the rigid reference member 2 may have an optical function. The outside surface of the reference member may have a smaller radius than is the predetermined curvature of reference surface 4. Thus, the reference member concentrates the fluorescent (or diffusely scattered) light into a selected direction where detector 22 is positioned. Alternatively, the reference member may be attached to an optical fiber that collects the fluorescent (or diffusely scattered radiation) and transmits the radiation to the detector.

Referring to both preferred embodiments, the system performs differential thickness measurements. At any instant of time, camera 22 of detection system 5 detects intensity of radiation arriving from a point which is located between the measured corneal surface and known reference surface 12. This intensity of the fluorescent or diffusively reflected radiation is dependent on the local thickness of the mixture of fluids compressed between the two surfaces at that point. The detection system scans an area of approximately 5 mm$^2$ of reference member 2 and forms a large number of adjacent pixels (surface regions of the smallest resolution) containing the intensity information for the related locations. Digitizer 24 digitizes the detected intensities, and stores the three dimensional sets into the memory of computer 26. Each pixel has x,y coordinates and a thickness value computed from the intensity of the detected radiation. The x,y resolution of the system of a preferred embodiment is about 50 μm.

From this data, with suitable compensation for the selected geometry of the system, computer 26 creates a model of the detected thickness, and incorporate to the model the curvature of reference surface 4 to create a model of the measured corneal surface. This is preferably performed by fitting the detected data to a two dimensional polynomial and adding the resulting topography to the topography of the rigid reference surface 4. The resulting topography represents the measured corneal surface. This differential topography measurement can have resolution of a few micrometers.

Figure 4A:
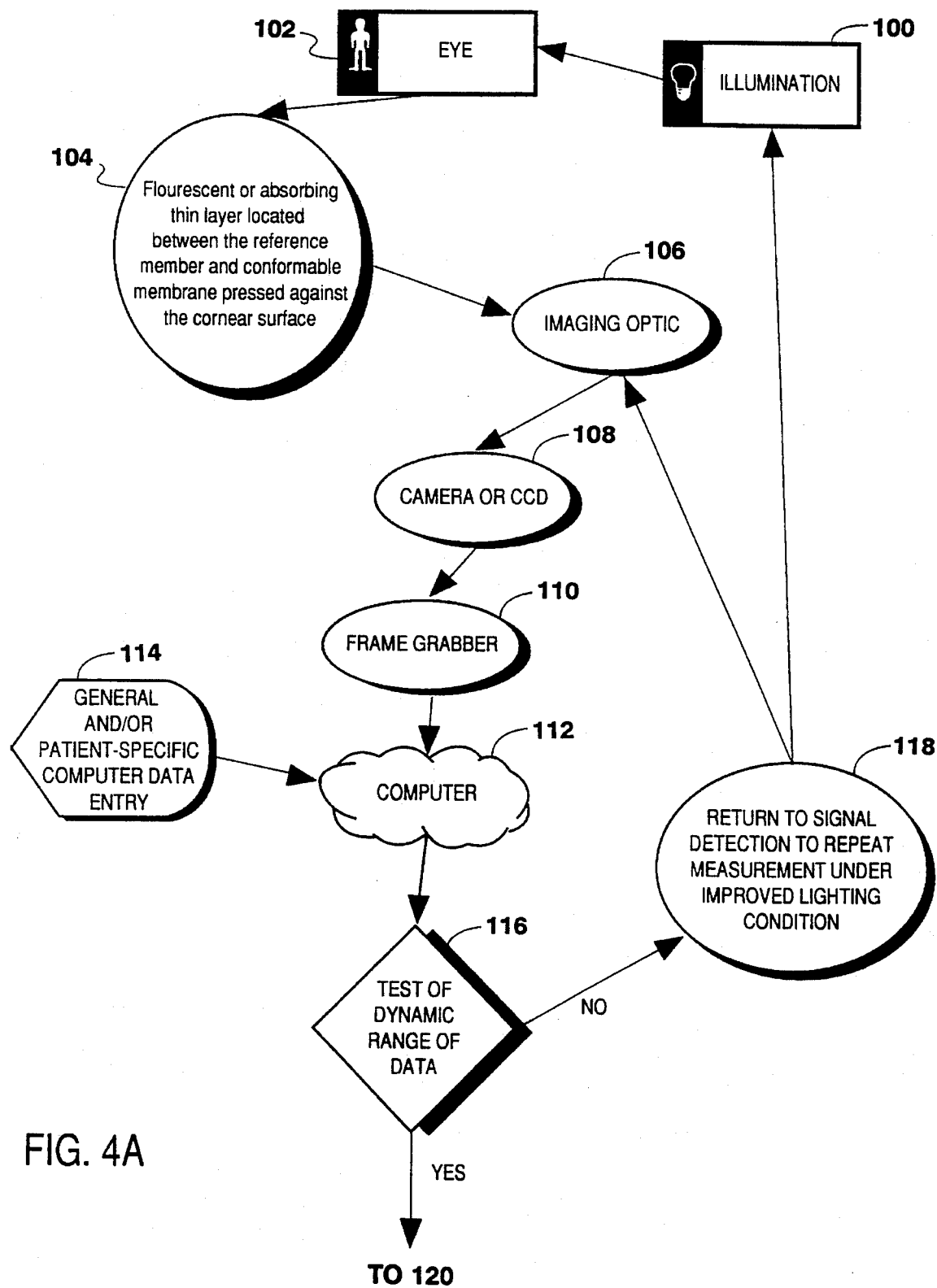
FIGS. 4A and 4B show a flow diagram describing operation of the topographers.
Figure 4B:
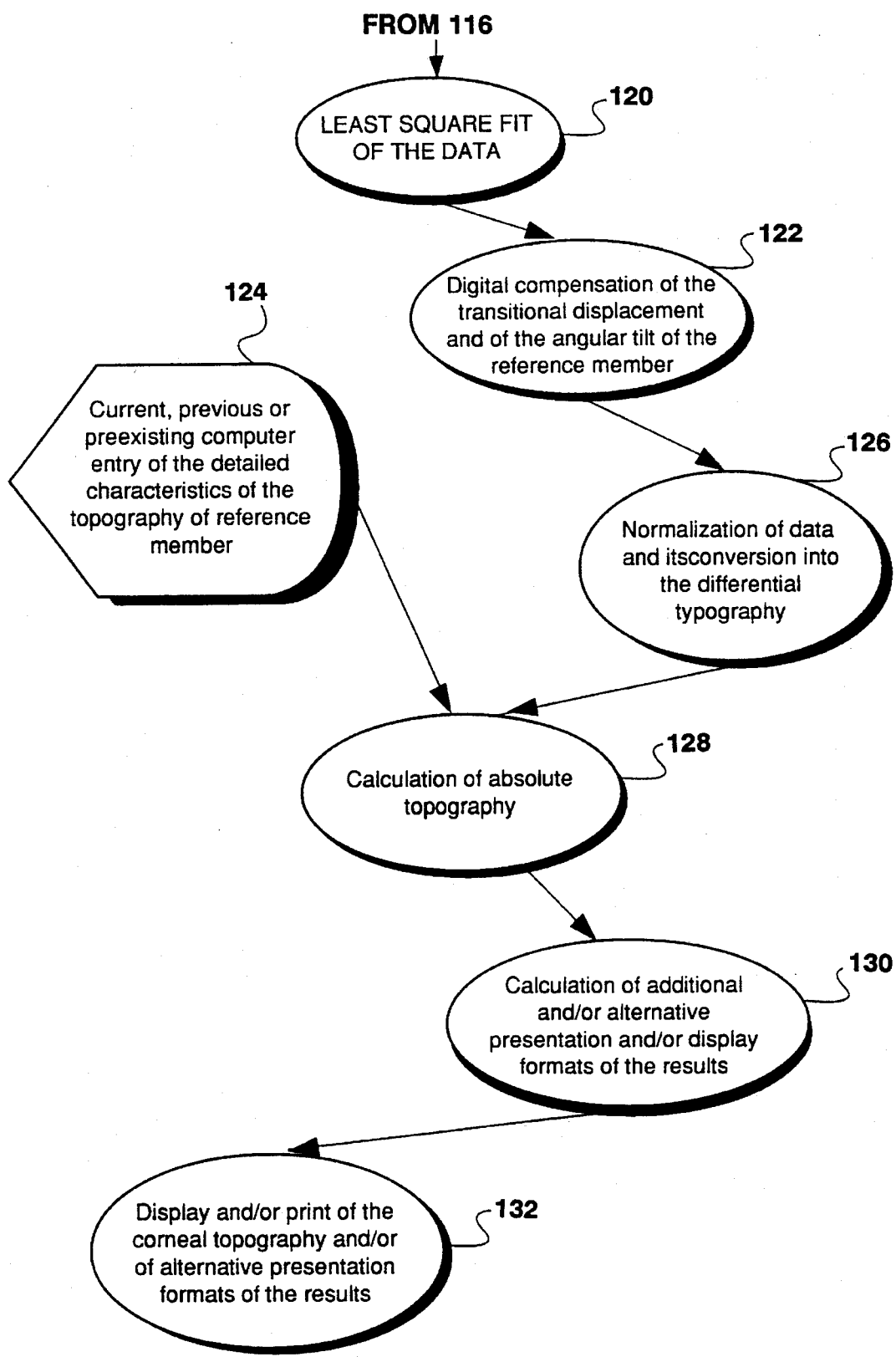

FIGS. 4A and 4B schematically show the operation of the topographer. Referring also to FIG. 1, rigid transparent reference member 2 with conformable membrane 13 containing a fluorescent (or absorbing) fluid is pressed against the corneal surface (104). The light source 3 directs light 17 onto reference member 2. The imaging system 106 focusses returning signal 19 onto camera 22, or in FIG. 4A, camera or CCD 108. In steps 108, 110, and 112, the returning light is detected, digitized and saved frame-by-frame in the memory of computer 26 (112 in FIG. 4A). The computer governs the whole process, receives general and/or patient specific data (114), tests the detected data (116) and rejects unreliable data. If the dynamic range of the signal is wrong, the computer initiates another measurement under improved lighting conditions (118). The computer performs fitting of the data (120). The fitted data are manipulated to eliminate errors caused by translational displacement or an angular tilt (122). Then, the topography data (126) are compared to the reference topography data (124) that represent reference surface 4 and the corneal topography is determined (128). The calculation can also take into account patient specific data, for example, previous corneal topography measurements. The corneal topography is then displayed (132).

Figure 5:
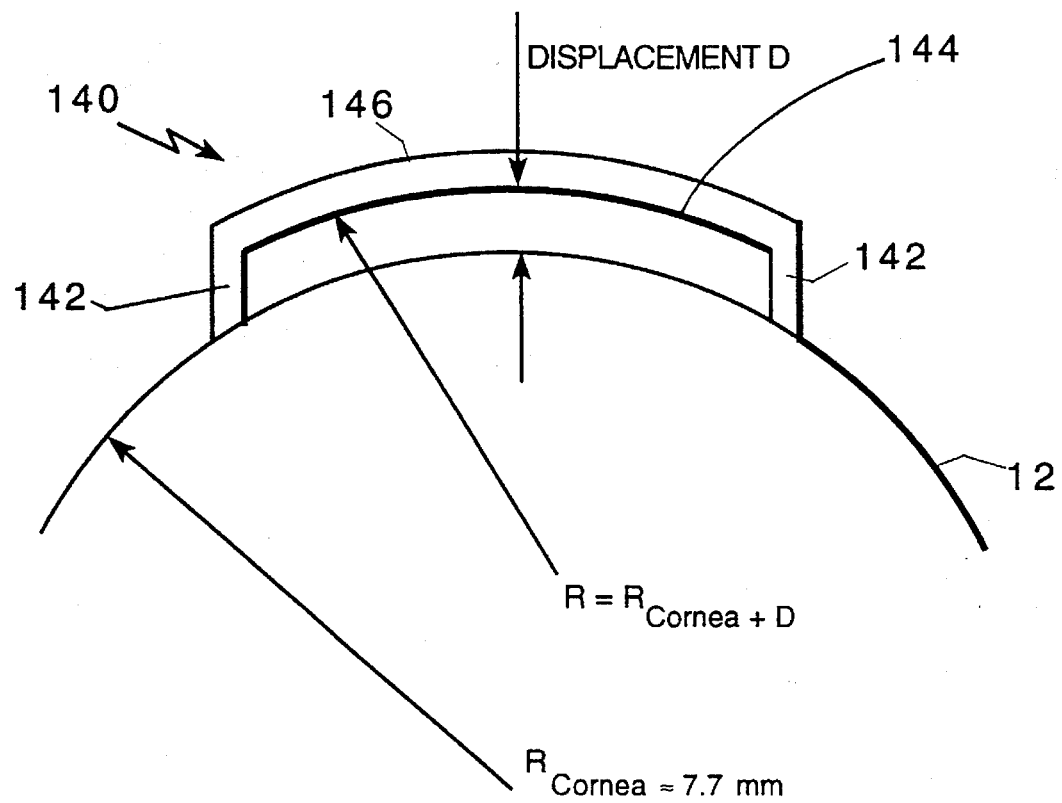
FIG. 5 is a diagrammatic cross-sectional view of a reference eye contact system without a conformable substance.
Figure 5A:
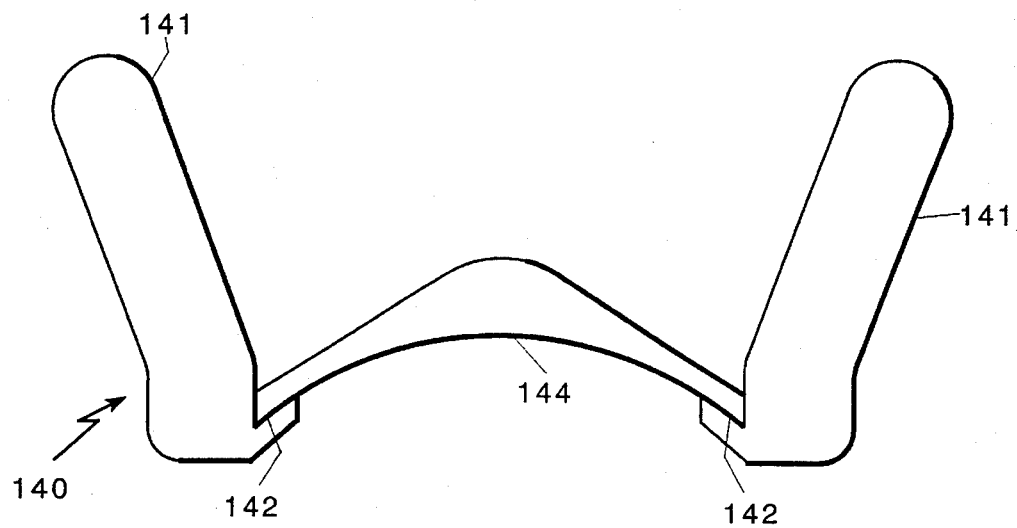
FIGS. 5A and 5B show diagrammatically the reference system of FIG. 5 adapted for practical application onto the eye.
Figure 5B:
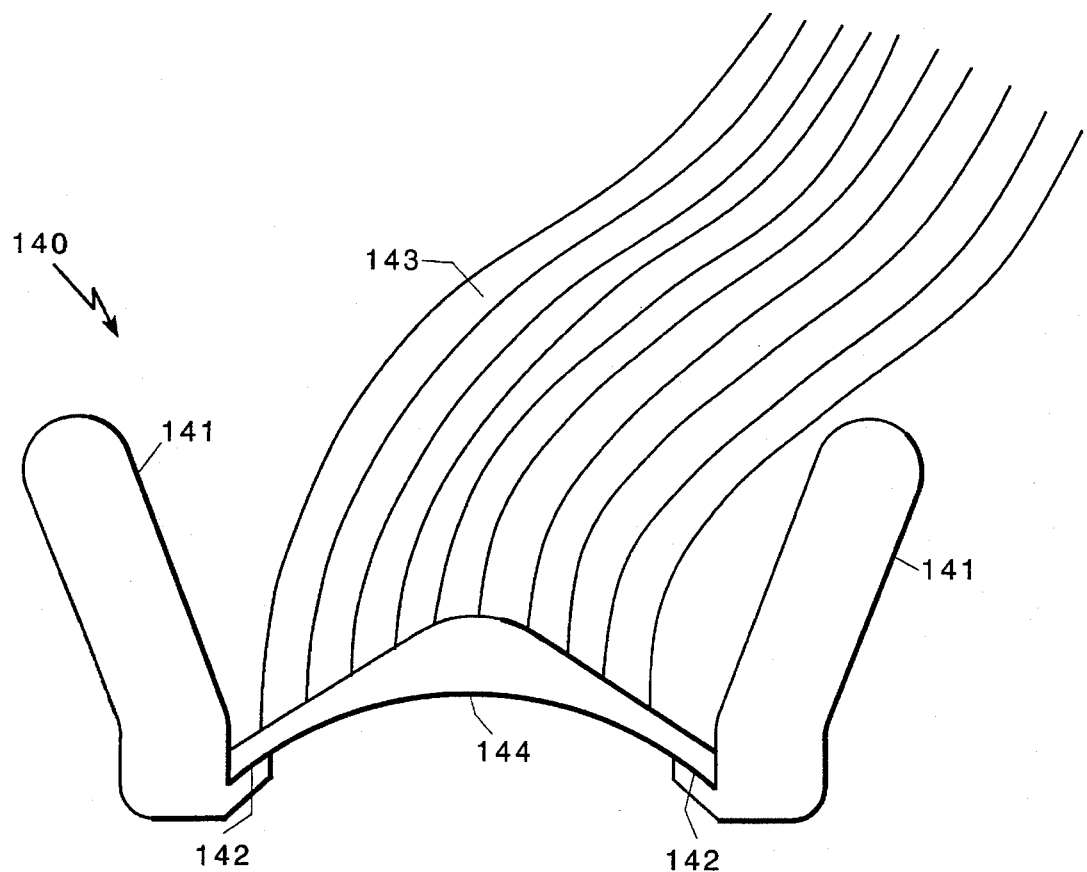

Another type of the corneal reference system is shown in FIG. 5. Reference member 140, made again of an optically transparent material, does not include the conformable substance held in the pliable barrier as is described for the embodiments of FIGS. 1 through 3. Rigid reference system 140 is applied temporarily onto the surface of the eye like a "contact lens" for the purpose of taking measurements of the corneal topography. Reference member 140 may include an applicator 150 or may also be attached to an optical fiber bundle 143 as shown in FIGS. 5A and 5B, respectively. To examine the corneal topography at different locations, the introduced light is coupled sequentially to the individual fibers. Alternatively, the single optical fiber is applied to different locations.

Referring to FIG. 5, reference member 140 contacts the corneal surface 12 using a spacer ring 142 located on the periphery of reference member 140 and outside of the measured region of the corneal surface. Spacer ring 142 is designed to maintain a substantially constant displacement, D, between the corneal surface 12 and a reference surface 144. The curvature of reference surface 144 is approximately equal to the expected eye curvature (i.e., 7.7 mm) plus a displacement value, D. For practical purposes, the displacement is less than 5 mm. A compact fluid exchange system (not shown in the figure) may be connected to the reference member to facilitate introduction or removal of fluid from the displacement space between the corneal and reference surfaces.

Reference member 140 is used for referencing the measured data to reference surface 144. The various measurement systems are employed to measure local displacement $D_{xy}$ that depends on the curvature variation of the measured eye from the selected curvature of reference surface 144. For embodiments wherein reference member 140 can be mass-produced relatively inexpensively (e.g., by injection molding), spacer ring 142 is integrally connected to the reference member. For embodiments wherein production of reference member 140 is relatively expensive, the reference member is reusable and spacer ring 142, detachably connected to the reference member, is a disposable part of they eye contact system. In either case, the performance of the reference member may be calibrated against a precise standard. The calibration values are stored in the system's processor and are used to adjust the measured data. Reference member 140 is used in combination with different optical techniques such as optical coherence-domain reflectometry (see for example, Youngquist et al., *Optical Letters* Vol. 12, p. 158, 1987; Hee et al., *Journal of Opt. Soc. Am. B* Vol. 9, p. 903, 1992), wavelength-multiplexed interferometry (see for example, Williams et al., *Optics Letters*, Vol. 14, p. 542, 1989), white-light interferometry (see for example, Flournoy et al., *Applied Optics*, Vol. 11, p. 1907, 1972; Lin et al. in "White light Interferometry", IBM J. Res. Development, p. 269, May 1972) for determination of the displacement $D_{xy}$.

Figure 6:
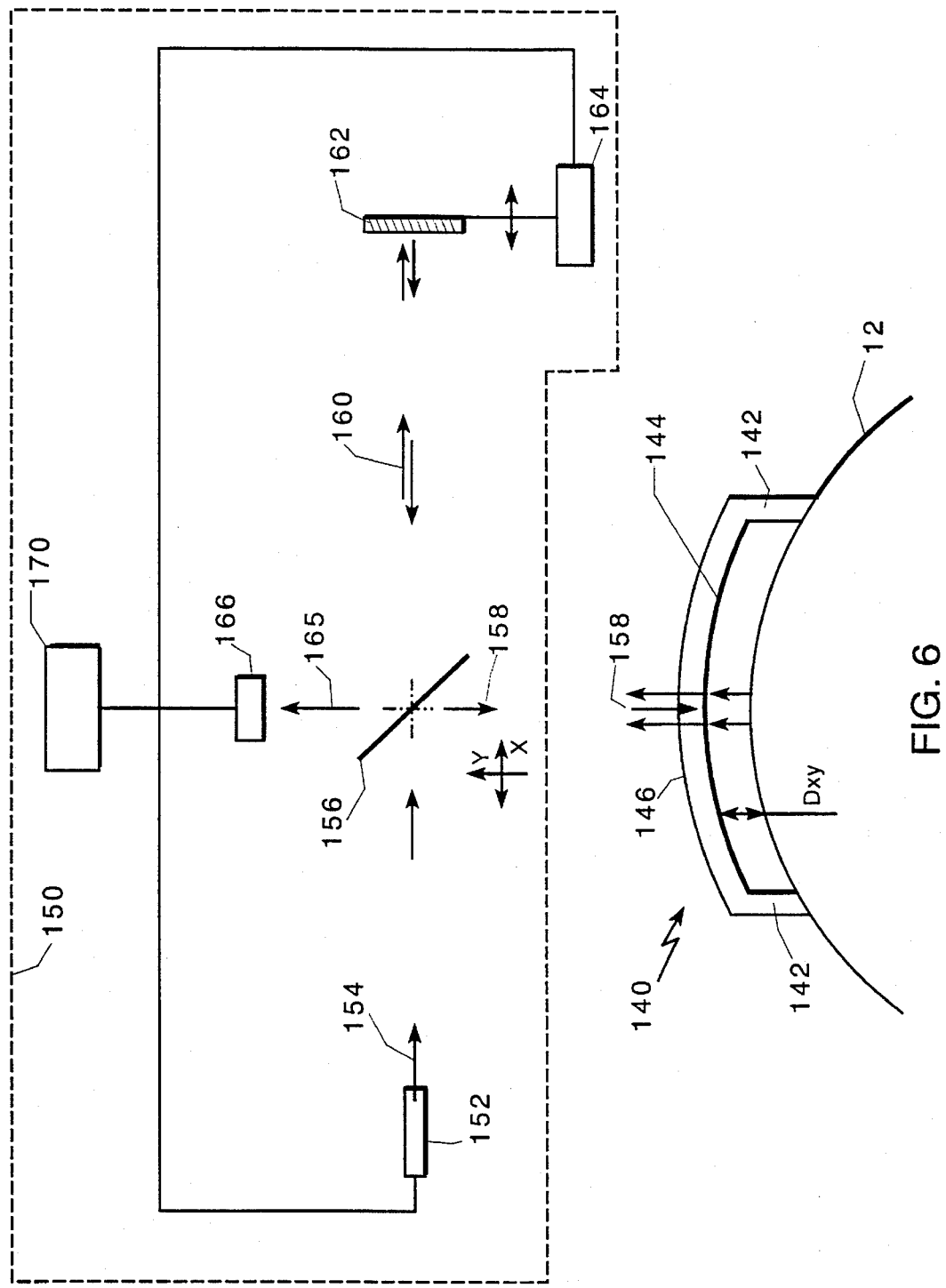
FIGS. 6 and 7 are diagrammatic views of the corneal topographer utilizing the reference system of FIG. 5 and an interferometric system.

Referring to FIG. 6, in another preferred embodiment, a Michelson interferometer 150 is used to measure $D_{xy}$ across the area of interest. This interferometer is similar to the experimental system described by Youngquist et al. A laser source 152 emits a spatially coherent beam 154 that is partially reflected, partially transmitted by a beam splitter 156. A reflected beam 158 is incident onto outer surface 146 of the reference member. (For simplicity, the angle of incidence is shown to be 90°). Beam 158 encounters interfaces 146, 144, and 12 and is partially transmitted and partially reflected back to beam splitter 156.

Beam 160, transmitted through beam splitter 156 is reflected of a vibrating reference mirror 162 driven by a piezoelectric transducer 164. Oscillating reference mirror 162 modulates the second leg (i.e., pathlength) of the interferometer and is used for a heterodyne detection scheme that reduces the noise effects. Reflected beams 160 and 158 are recombined (165) and directed to detector 166. The detected signal is processed by an analyzer 170. System 150 detects the fundamental modulating frequency that displays a maximum when the optical paths of beams 158 are equal to path 160 governed by moving mirror 162, i.e., interference fringes occur when the a time delay of path 160 is equal to any one of the three time delays associated with beams reflected from surfaces 146, 144 or 12. Detector 166 outputs a maximum signal when any two optical waves have their phases in quadrature (i.e., constructive interference). Analyzer 170 preferably measures the amplitude of the fundamental frequency and plots the amplitude as a function of the vibrating mirror displacement. The resolution of the system (i.e., the peak width) depends on the spatial coherence of the introduced beam (154). The plot of the amplitude vs. the mirror displacement includes three dominant peaks coming from surfaces 146, 144 and 12, depending on the index of refraction of the corneal surface (i.e., the epithelium and the tear fluid, or stroma, or the Bowmans layer after performing a partial refractive keratotectomy) and the index of refraction of the rigid reference member. For the topography measurement, the system is adjusted to measure the distance $D_{xy}$ between the peaks associated with reference surface 144 and the corneal surface 12. If surface 146 is covered with an antireflective coating, there is no reflection of this surface, and the system measures only the other two peaks. The system scans over the region of interest to determine $D_{xy}$ for a desired number of measured points and then determines the corneal topography using the measured set of $D_{xy}$ numbers similarly as described in FIGS. 4A and 4B.

Figure 7:
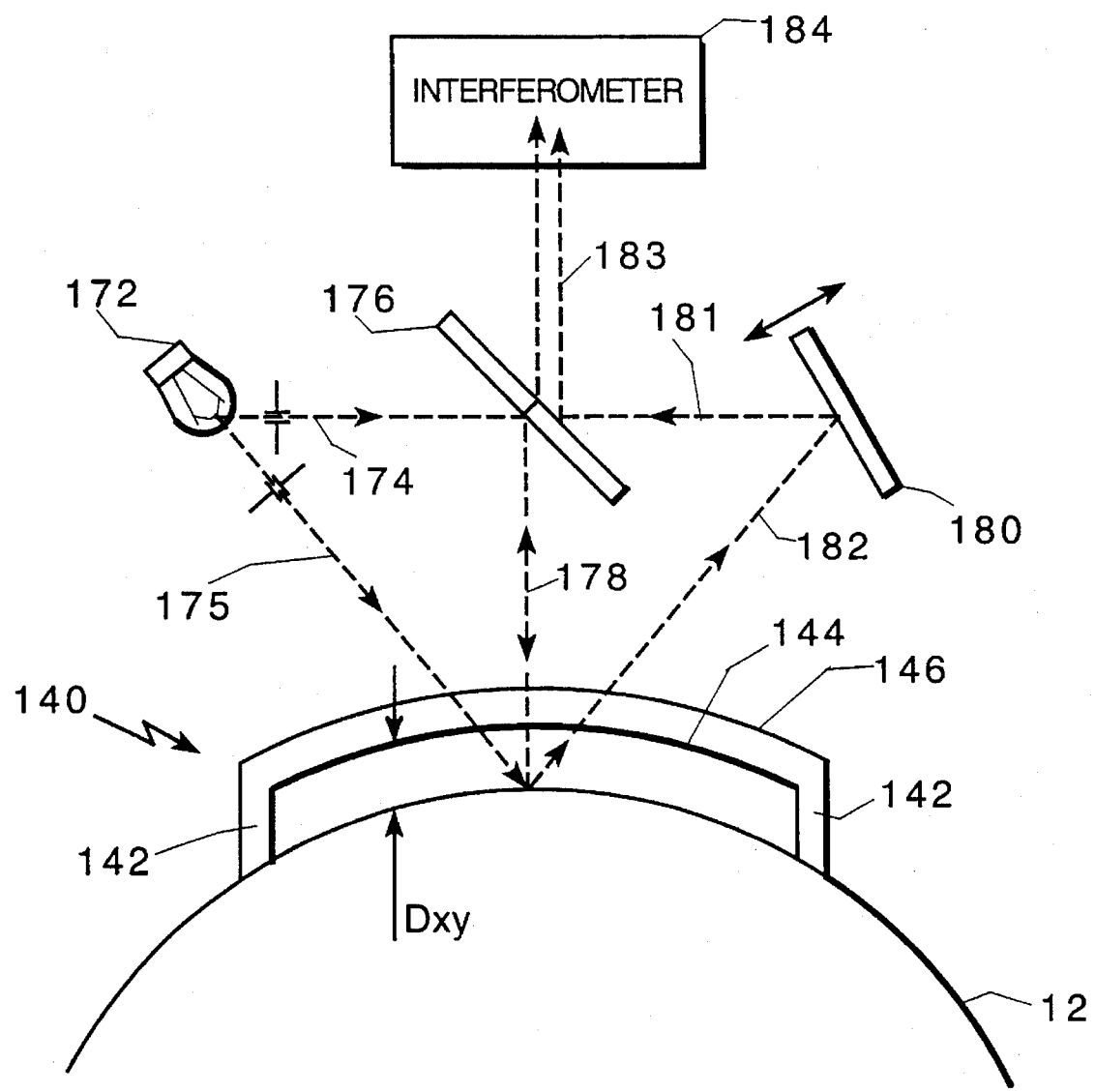

In another embodiment a white light source is used in system of FIG. 7 that is a modification of the Michelson interferometer. the system uses two light beams 174 and 175 generated by the same source 172. The white light fringes appear only when the optical path difference from surfaces 146, 144, and 12 of the first branch of the interferometer and a surface 200 of the second branch. For precise interferometric measurements it is useful to know precisely the angle of incidence, the refractive index of the examined material and its wavelength dispersion, the mirror position, and the measurement is also affected by the reflecting surfaces and possible haze above the surfaces. The system of FIG. 7 utilizes two independent sets of interferometric branches to measure thickness $D_{xy}$ at a selected location 171. The refractive index of the rigid reference member is known. The first incident beams 175 is directly directed to reference member 140 and the second beam 174 is directed to a beam splitter 176 that partially reflects the incident beam to create a beam 178 and partially transmits the beam into the 183 direction. Incident beam 175 is partially reflected and partially transmitted to the epithelium surface 12 and reflected back to a mirror 180. Beam 181 is reflected from mirror 180 which has adjustable position to create desired time delay (i.e., interferences fringes), and them beam 181 is further reflected by beam splitter 176 to interferometer 184. Beams 175 and 182 travel an additional optical path proportional to the thickness of the rigid reference member and the distance between the reference surface 144 and the corneal surface 12. By moving mirror 180 by exactly the same amount to create the same time delay, produces white light interference at the detector of interferometer 184. The mirror position is again measured to directly determine $D_{xy}$ spacing. The set of $D_{xy}$ data is again accumulated for different locations of reference surface 144 by scanning the reference surface in a circular motion. The $D_{xy}$ data is then used to determine the corneal topography as described above.

Alternatively, the interferometer uses optical fibers that facilitate propagation of the introduced and reflected light. The variation of the light path may be achieved by slight altering the fiber length, for example, by tightly wrapping the fibers around an oscillating piezoelectric crystal. Alternatively, the interferometer can scan the wavelengths of light to determine position of the mirror.

The present invention envisions the use of numerous other optical techniques for measurement of the $D_{xy}$ distances (e.g., High precision position sensing using diode laser radar techniques as described by Abbas et al. in *Laser-Diode Technology and Applications II*, SPIE Vol. 1219, p.468, 1990; Ranging technique with coherent optical radiation using a phase shift method as described by Grattan et al. in *Laser-Diode Technology and Applications II*, SPIE Vol. 1219, p.480, 1990)

Figure 8:
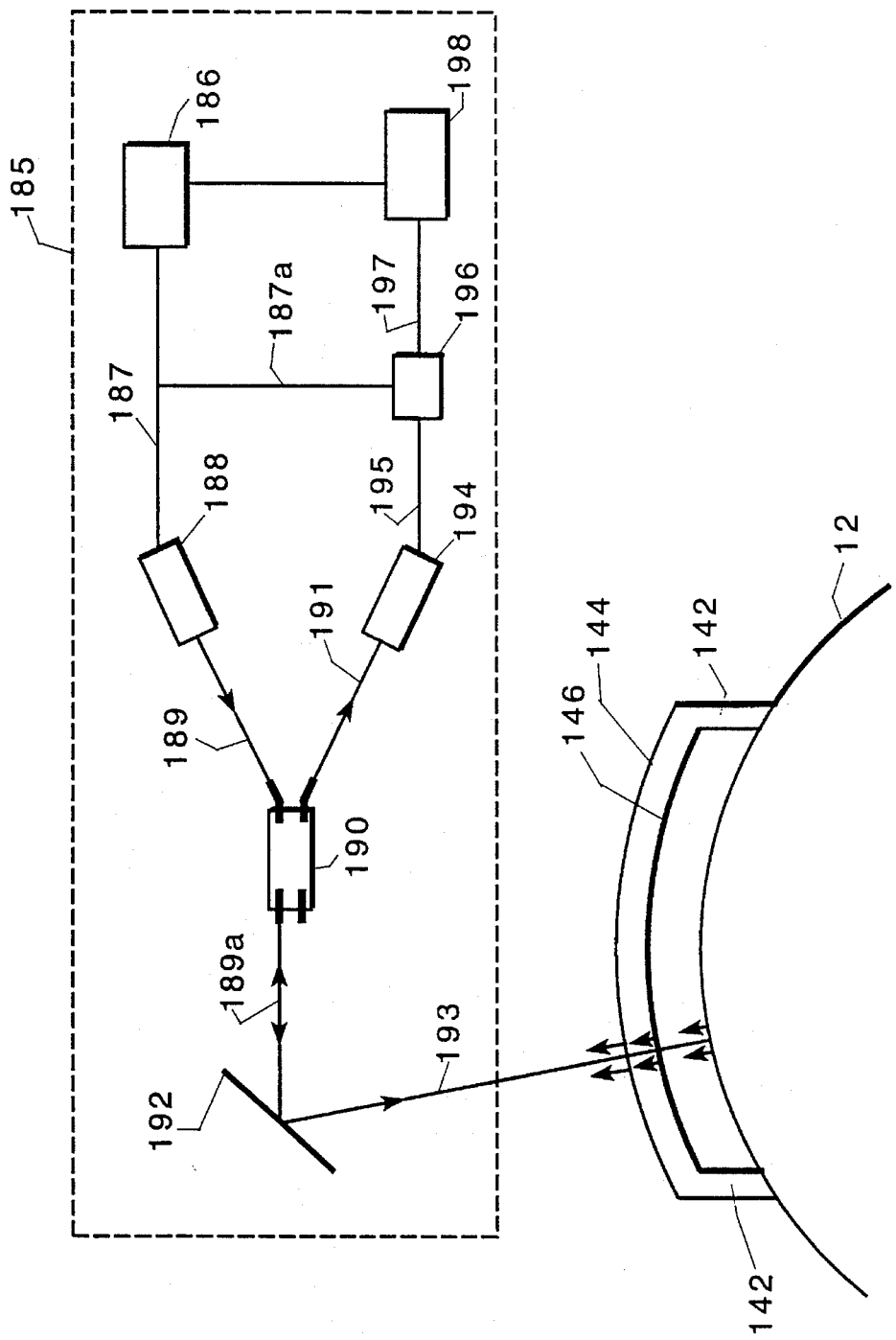
FIG. 8 is a diagrammatic view of the corneal topographer utilizing the reference system of FIG. 5 and an optical position sensing system.

Referring to FIG. 8, in another preferred embodiment, a laser radar system 185 measures the $D_{xy}$ spacing by detecting reflections from surfaces 12 and 144 using a frequency chirped, intensity modulated laser beam. The system includes a laser 188 driven by a RF chirp source 186, a directional fiber optic coupler 190, a scanning mirror 192, a light detector 194, a mixer 196, and a processor 198. Laser 188 emits a frequency chirped, intensity modulated light beam (189) that is coupled to fiber optic coupler 190 having a 50% coupling ratio. The output (189*a*) from directional coupler 190 is focused by a lens system onto a set of scanning mirrors 190 and is delivered perpendicularly to a selected location (x,y) of surface 146 of rigid reference member 140. The incoming beam (193) is reflected from surfaces 146, 144, and 12 and travels back to fiberoptic coupler 190. The coupler output beam 191, which is the sum of at least three delayed, overlaying waveforms of the introduced beam 189, is detected by detector 194. The RF detector output (195) is mixed together with the original frequency chirped waveform (187*a*) in mixer 196. Mixing of the introduced chirp (187) and reflected chirp (195) results is a number of frequencies proportional to the distances of the reflecting surfaces since the round-trip time delay is much shorter than the duration of the chirp. The system uses a chirp of a bandwidth of few gigahertz and duration of on the order of millisecond. The intermediate frequency from mixer 196 is Fourier transformed by processor 198 to determine frequencies of the reflections from the individual surfaces 146, 144, and 12. In the intermediate frequency spectrum, the frequency peaks of reference surface 144 and the corneal surface 12 are resolved to determine the $D_{xy}$ distance. Laser 188 is selected to produce a wavelength that has a sufficient reflection from the corneal surface 12, and the power of the emitted light is on the order of few milliwatt. Scanning mirror system 192 scans beam 193 over the entire area of interest to measure the $D_{xy}$ data.

Figure 9:
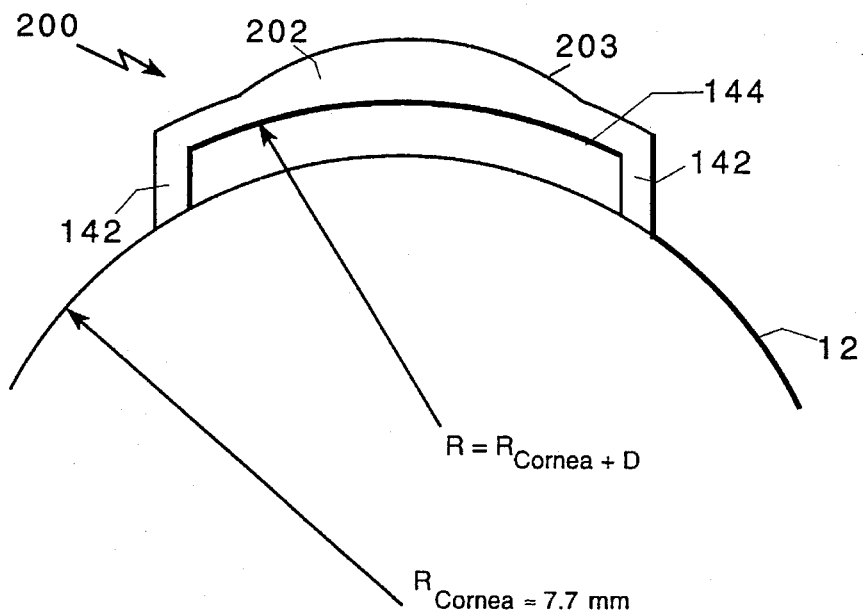
FIG. 9 is a diagrammatic cross-sectional view of the reference system of FIG. 5 further including an optical lens.
Figure 9A:
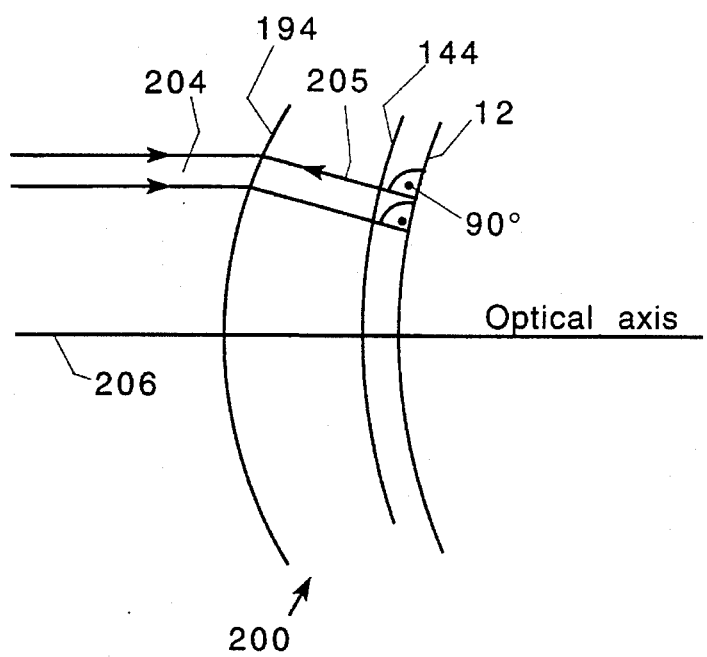
FIG. 9A shows diagrammatically the optical function of this lens.

Referring to FIG. 9, another type of the rigid reference member is designed to have optical function. Reference member 200 again includes a spacer ring 142 adapted to maintain a substantially constant displacement, D, between the corneal surface 12 and reference surface 144. A lens 202 is formed by shaping outside surface 203 to have a smaller radius than reference surface 144. The optical power of lens 202 is designed to compensate for the eye curvature. The operation of reference member 200 is illustrated in FIG. 9A. The system's light source emits light parallel to axis 206. Parallel rays 204 of an incoming light beam enter reference member 200 and are refracted at an angle corresponding to the lens power. Refracted rays 205 strike an ideal corneal surface 12 at a 90° angle and are partially reflected from the eye surface. In this case, the reflected rays return exactly on the path of incoming beam 204 and are detected. However, when the corneal curvature deviates from the expected "model" curvature, beam 205 is reflected at a different angle than 90°. This beam deviation, directly dependent on the actual corneal curvature.

Figure 3A:
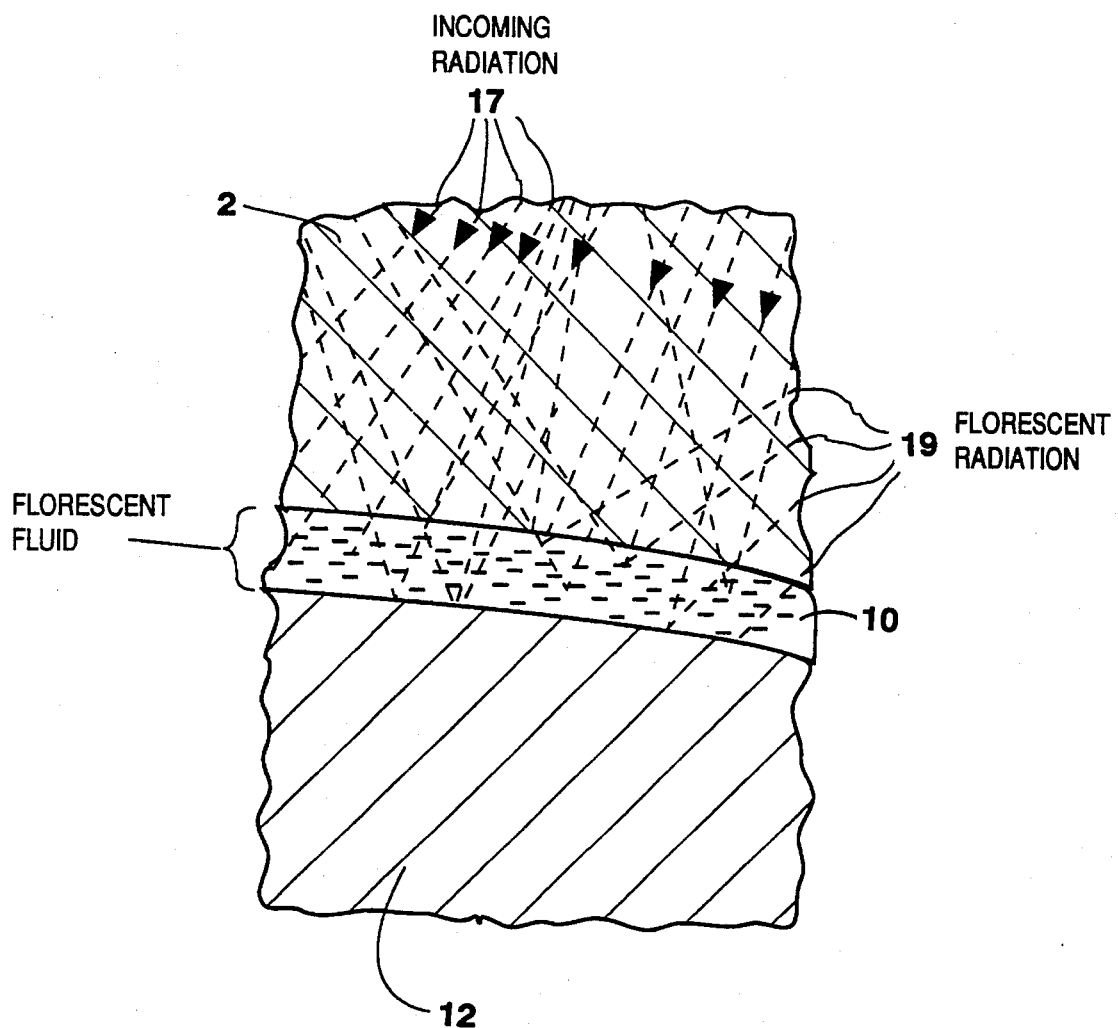
FIG. 3A is an enlarged section of FIG. 3 diagrammatically showing the first preferred embodiment using fluorescent measurements.
Figure 3B:
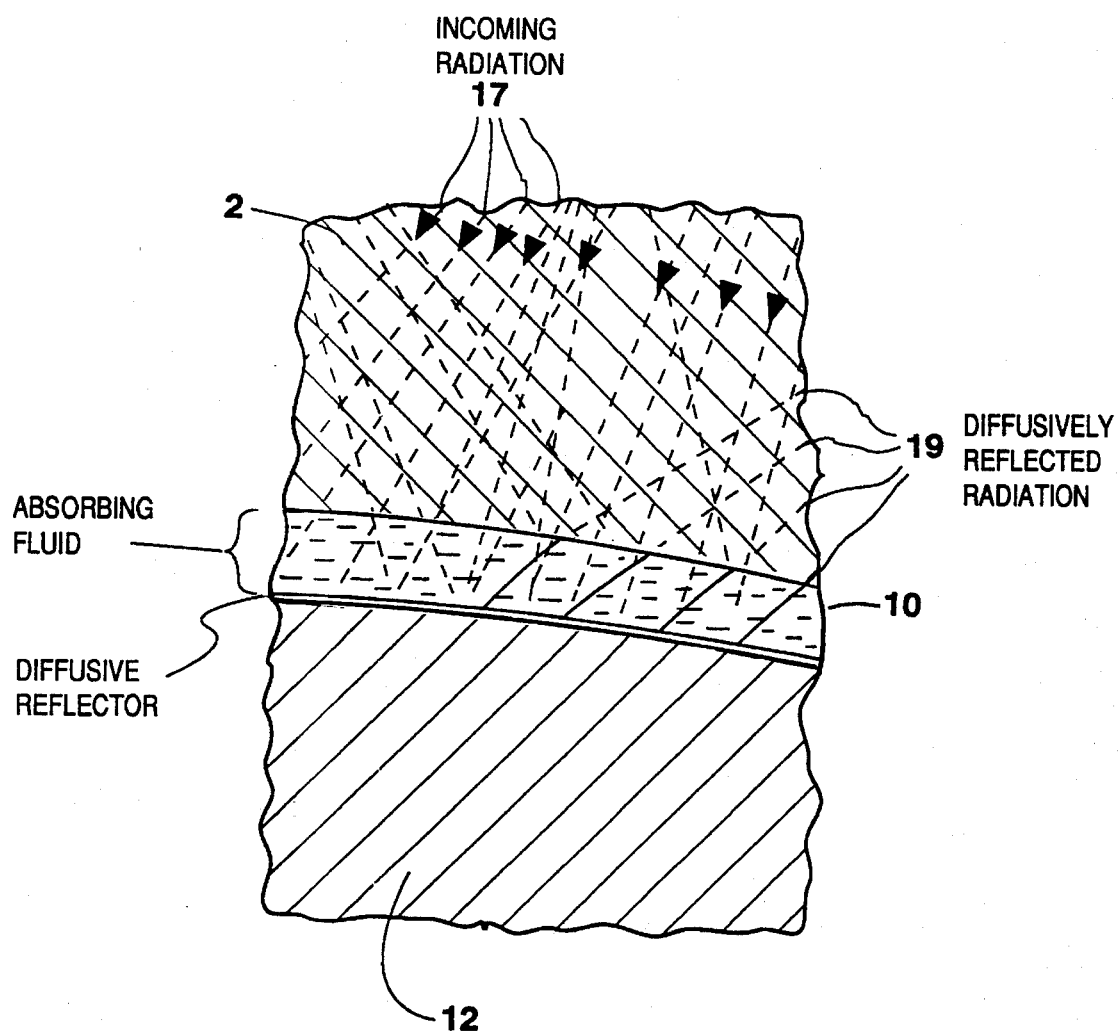
FIG. 3B is an enlarged section of FIG. 3 diagrammatically showing the second preferred embodiment using absorption measurements.

Reference member 200 may be adapted for use in conjunction with the embodiments of FIGS. 3A and 3B or, alternatively, may be used in conjunction with standard deflectomertic techniques (for example, rasterography, deflectometry or moire deflectometry) to determine the corneal topography directly. Reference member 200 directs most of the light reflected from the corneal surface back to their original direction; thus the detector can detect more reflected light by scanning a smaller area. The directional properties of the reflected light directly depend on the curvature of the eye. In these measurements, the measured data are not referenced to reference surface 144 as is done for the above-described embodiments. Alternatively, a set of Fresnel lenses or holographic lenses may replace lens 202.

Figure 10:
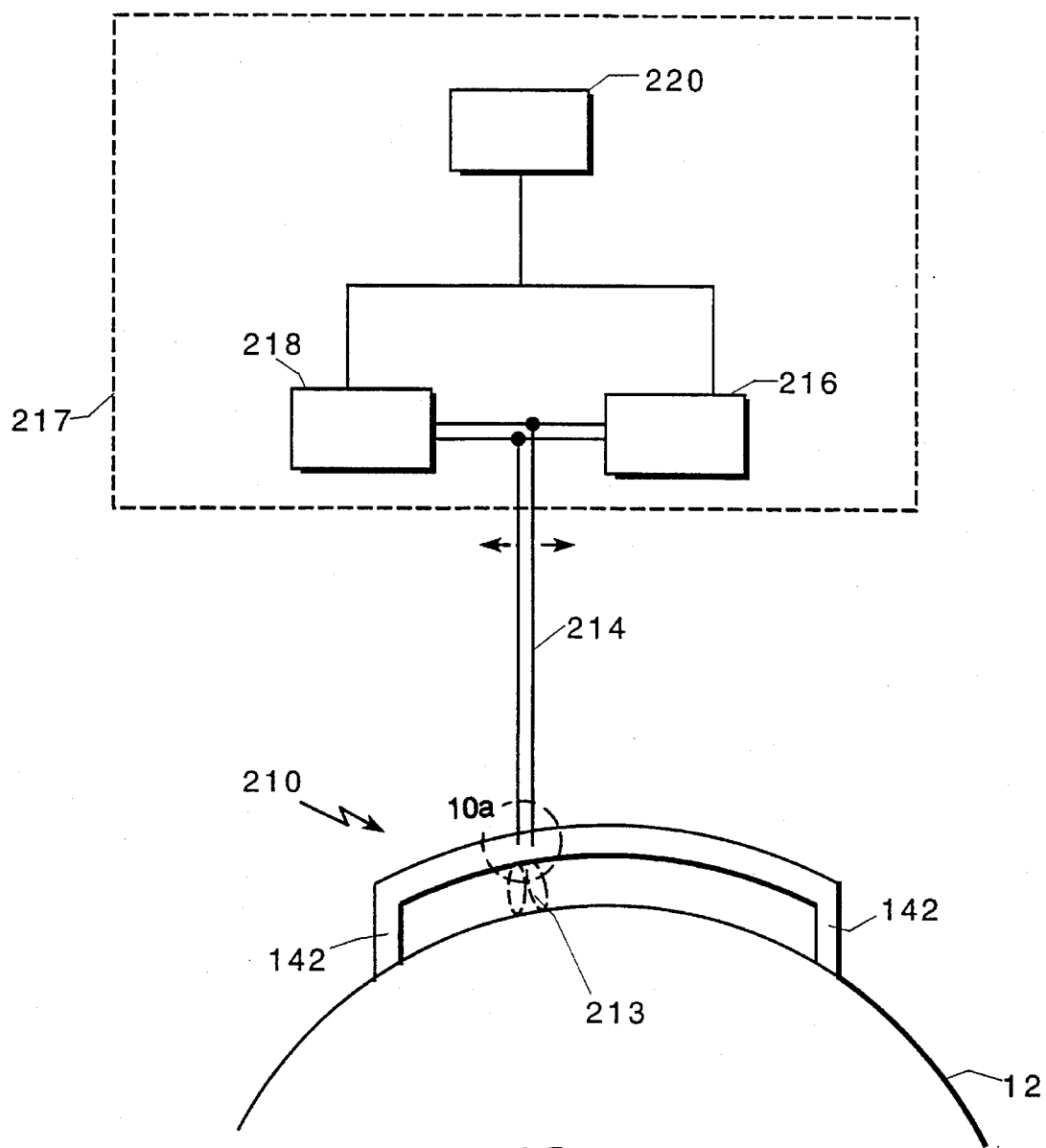
FIG. 10 is a diagrammatic view of the corneal topographer utilizing the reference system of FIG. 5 adapted for acoustic measurements.
Figure 10A:
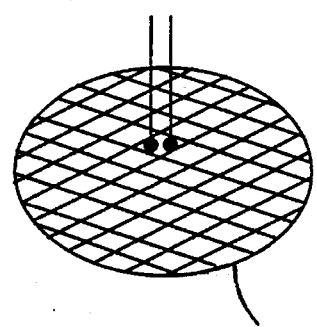

Referring to FIG. 10, in another preferred embodiment, the rigid reference system of FIG. 5 is adapted for acoustic measurements. Reference member 210 the reference surface modified to include an array of discrete acoustic transducers 212. The reference surface formed by array 212 is again displaced by distance D from the corneal surface 12 using ring 142. The individual transducers (i.e., acoustic sources and microphones) of array 212 are of about 200 nm to 600 nm in size and are fabricated photolithographically. Each transducer is contacted by two leads 214 adapted to excite the transducer at desired acoustic frequencies and to detect the reflected waves in individual regions 213. For simplicity FIG. 10 shows leads 214 contacting the transducer from the top in a movable manner; however, in a practical array the transducers may also be contacted by a set of conducting lines deposited between the transducers. These line leads end at the boundaries of array 212 where the are contacted in a standard manner. A processor 220 governs the operation of ultrasonic system 217. Transmitter 216 activates a selected transducer to generate an acoustic wave of a desired frequency in the kHz range. The reflected wave is detected and processed by a receiver 218. For each transducer, transmitter 216 scans a range of frequencies to detect a fundamental acoustic frequency ($f_s$) at which a standing wave is created in regions 213. For this frequency, processor 220 calculates $D_{XY}$ ($D_{XY}=2v/f_s$; wherein v is the sound velocity) and correlates measured $D_{XY}$ with the location of the transducer. Ultrasonic system 217 measures the set of the $D_{XY}$ data and then determines the topography of the eye by accounting for the shape of the reference surface as described above.

Figure 11:
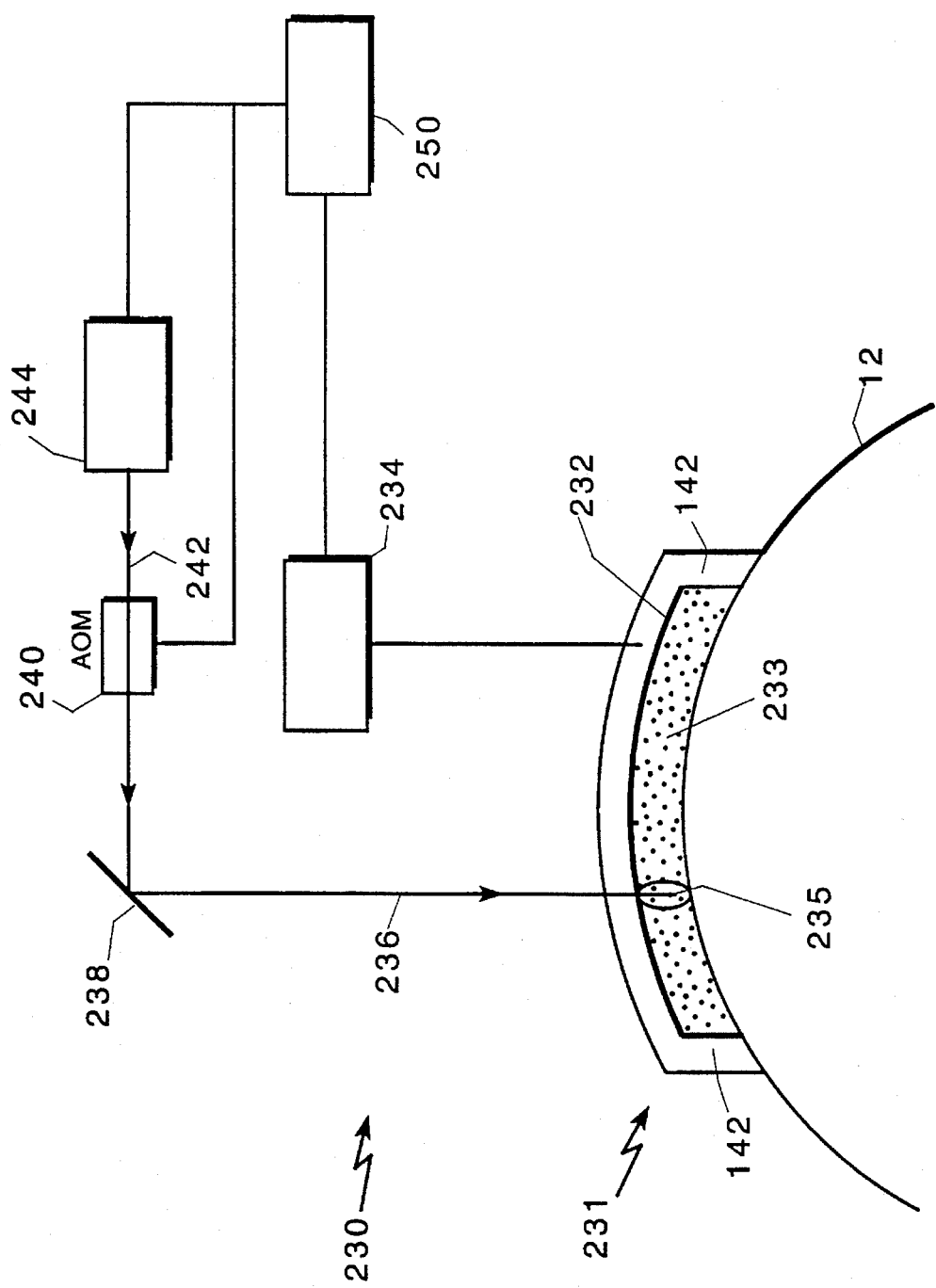
FIG. 11 is a diagrammatic view of the corneal topographer utilizing the reference system of FIG. 5 adapted for acousto-optic measurements.

Referring to FIG. 11, another embodiment uses opto-acoustical method for determination of the local distance ($D_{XY}$) between the reference surface 144 and corneal surface 12. Opto-acoustical system 230 uses a laser beam 236 of a high monochromacity tuned to the absorption energy of water molecules 233 present between reference surface 144 and corneal surface 12 and modulated at a desired frequency. A considerable part of the modulated laser beam is absorbed and transformed to thermal energy that excites acoustic waves at the modulation frequency.

The system is governed by a processor 250 that controls a laser source 244, acousto-optic modulator 240, a mirror 238 and receiver 234. Laser 244 generates a laser beam 242 of a wavelength in the infrared region selected to be absorbed by vapor molecules 233. Beam 242 is modulated at a desired frequency (f) by acousto-optic modulator 240 and delivered to a selected location (x,y) of reference member 231 using mirror 238. Since the intensity of the laser beam is alternating at an acoustic frequency (f), the absorbed radiation excites acoustic waves of a corresponding frequency between surfaces 144 and 12. The acoustic wave is detected by a microphone (e.g., an optical Golay microphone, an inductive pickup, capacitive pickup, condenser, electrodynamic or electret microphone). In a preferred embodiment, reference member 231 forms a resonant chamber with the microphone located on reference surface 232 and connected to receiver 234. Acousto-Optic modulator 240 scans a range of frequencies to find a resonant frequency ($f_s$) for region 235 with (x,y) coordinates. From the resonant frequency, the displacement value $D_{XY}$ is calculated ($D_{XY}=2v/f_s$). Mirror system 238 is used to scan laser beam 236 over the entire area of reference member 231. The measured set of $D_{XY}$ data is used to determine the corneal topography.

Figure 12:
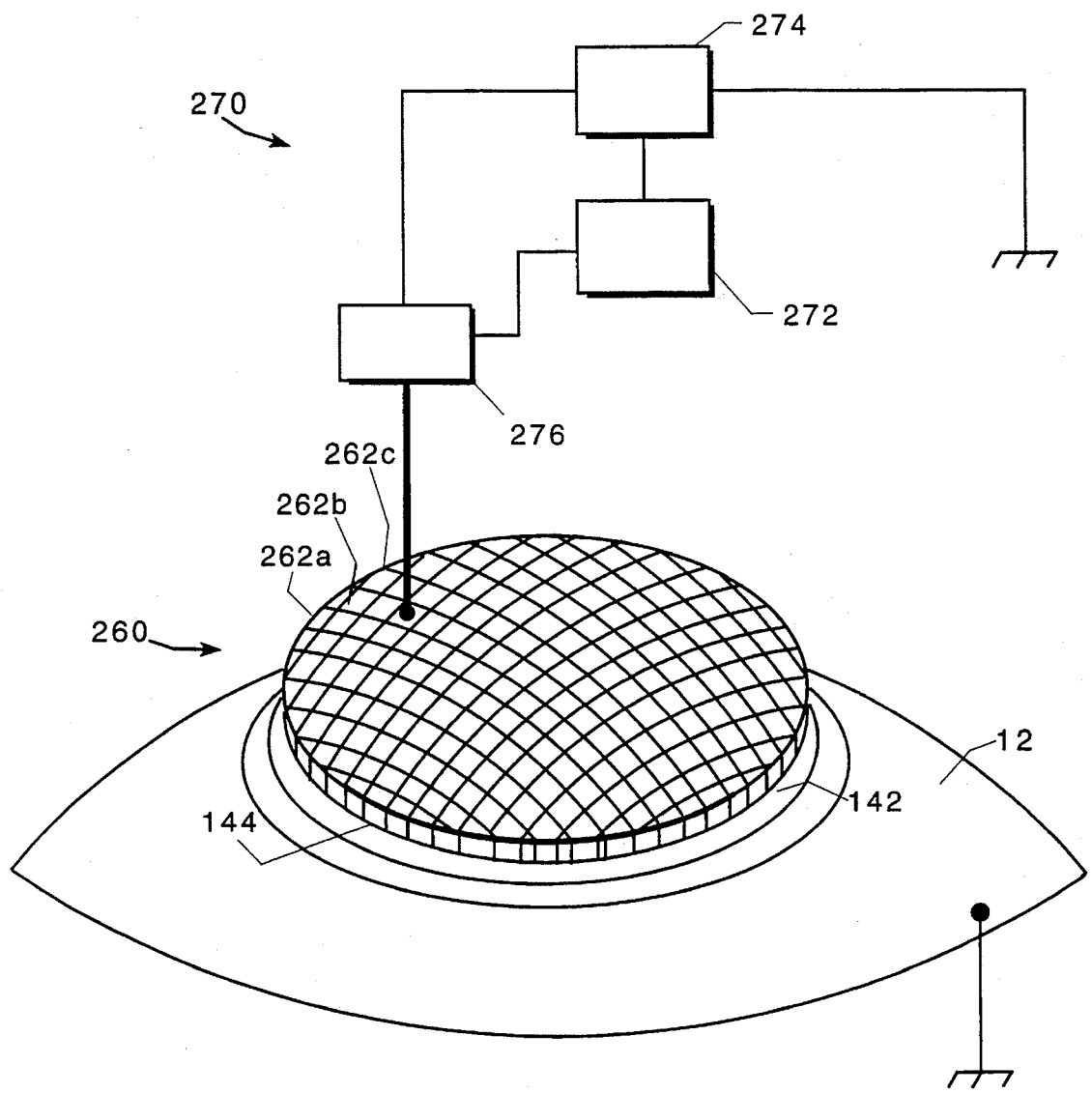
FIG. 12 is a diagrammatic view of the corneal topographer utilizing the reference system of FIG. 5 adapted to measure capacitively the corneal curvature.
Figure 12A:
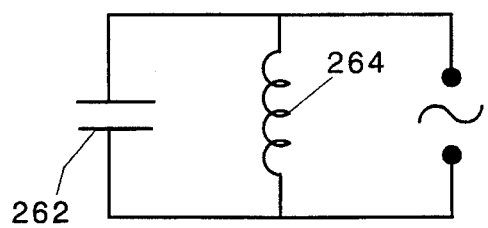
FIG. 12A schematically shows equivalent electrical elements of the reference system of FIG. 12.

Referring to FIG. 12, another embodiment of the present invention uses a capacitance technique for the corneal surface measurement. The embodiment uses a reference member 260 that includes an array of conductive elements 262 forming reference surface 144. Reference member 260 is applied to corneal surface 12 in a similar manner as the reference members shown in FIGS. 6 through 10. Each element 262 forms a capacitor with a corresponding region of the corneal surface located below and connected to ground by grounding any body part of the person being examined. The local distance, $D_{XY}$, between reference surface 144 and corneal surface 12, forming a capacitive element, is measured capacitively. An inductance is connected in parallel to each capacitor element as shown in FIG. 12A.

A capacitance system 270 includes a processor 272, an source 274, and a contacting system 276. Processor 272 selects an individual capacitor with coordinates (x,y) using contacting system 276 and directs the operation of source 274. Capacitance $C_{XY}$ of each capacitor element 262 is measured by detecting a resonance frequency of a small AC signal applied to the LC system. The corneal profile is determined by measuring the local distance, $D_{XY}$, which is proportional to capacitance $C_{XY}$. The measured set of $D_{XY}$ data is again referenced to the shape of reference surface 144 to determine the corneal topography as described above.

The topographer can be a separate system or can be incorporated into a surgical system to provide measurements of the corneal surface during corneal surgery. During an eye operation it is useful to establish a reference point on the surface of the eye. This point is needed to compare the shape of the surface before and after surgery. This can be done by marking a specific point which will be kept for the duration of the operation. The marking would be done using a dye and placing a dot on the eye surface. This will help the surgeon to know the proper orientation of the eye.

During an eye operation the eye are anesthetized, thus the patient will not feel any discomfort when reference member 2 is pressed to the eye surface. However, when the corneal topographer is used as a stand-alone unit, some patients might feel discomfort or pain when the reference member is applied to the eye surface. In these cases, the eye will be anesthetized before the reference member is applied.

Other embodiments are within the following claims:

I claim:

1. A system for determining information concerning the topography of a portion of the exterior surface of the eye, the system comprising:

a rigid reference member having a reference surface of predetermined shape for lying over said portion of the eye; said reference surface being positionable in close proximity to and directed toward the exterior surface of the eye, means for determining distance data between said reference surface and said exterior surface of the eye over a multiplicity of data points sufficient in number and spacing to represent the local topography of the surface of the eye, and means for determining the desired information concerning the topography of said surface of the eye from said distance data in reference to said predetermined shape of said reference surface.

2. The system of claim 1 wherein said reference surface of said rigid reference member is concavely shaped to approximate the surface of the eye to enable the space therebetween to have a thin cross-section over the examined portion of the eye, enabling small differences in topography of the eye surface to be detected as relatively large percentage changes in the distance between said reference surface and said eye.

3. The system of claim 1 wherein said rigid reference member is transparent to selected optical radiation and said means for determining said distance data comprises an optical detector for detecting said radiation passing through said rigid reference member.

4. The system of claim 3, wherein said transparent reference member is associated with light refracting means for substantially directing radiation passing through said transparent member.

5. The system of claim 3, wherein said detector comprises a camera sensitive to radiation received from said reference member.

6. The system of claim 3, including means for forming an image of detected radiation received via said reference member and for determining energy intensities at points in said image.

7. The system of claim 3 further including a light source system positioned and adapted to irradiate through said reference member the corneal surface of the eye, said optical detector constructed to scan an x,y area of said reference member to collect the passing through light with an x,y resolution on the order of about 50 μm, a filter for selecting the wavelength of the radiation detected by said detector a digitizer constructed and arranged to digitize said collected light of said portion of interest of the corneal surface and create digitized signal, said means for determining the desired topography including a computer arranged to receive said digitized signal and determine therefrom distance data between said reference surface and said portion of the corneal surface of the eye over a multiplicity of x,y data points sufficient in number and spacing to represent the local topography of the corneal surface of the eye relative to said reference surface, and said computer further arranged to determine the desired information concerning the topography of said portion of the corneal surface of the eye from said distance data corresponding to said x,y data points in reference to said predetermined shape of said reference surface.

8. The system of claim 7 wherein said reference surface of said rigid reference member is concavely shaped to approximate said portion of the corneal surface of the eye to enable the space therebetween to have a thin cross-section over the examined portion of the eye, enabling small differences in topography of the corneal surface to be detected as relatively large percentage changes in the distance between said reference surface and said corneal surface of the eye.

9. The system of claim 8 in which the computer is programmed to fit the digitized data to a polynomial, said polynomial containing low order terms representing translational displacements, offset, and angular tilting of said rigid reference member relative to said eye surface, said polynomial also containing higher-order terms representing information about the topography of the eye.

10. The system of claim 3, wherein said detector comprises a lens for receiving radiation through said reference member, a camera upon which the lens focusses an image of said radiation, said camera adapted to produce analog intensity signals, and a frame grabber for producing digital signals from said analog signal for computer analysis.

11. The system of claim 3, further comprising means for digitizing said data, means for calculating a data polynomial by fitting said digitized data to a polynomial, means for providing detailed reference surface topography information, and means for combining said data polynomial with said reference surface topography information to provide information about the topography of the eye.

12. The system of claim 1 wherein said means for determining said distance data are optical means.

13. The system of claim 12 wherein said reference member is transparent to selected radiation and said optical means is a white light interferometry system adapted to determine said distance data.

14. The system of claim 12 wherein said reference member is transparent to selected radiation and said optical means is a single color interferometry system adapted to determine said distance data.

15. The system of claim 12 wherein said reference member is transparent to selected radiation and said optical means is a laser radar (ladar) system adapted to determine said distance data.

16. The system of claim 1 wherein said reference member further comprises an array of conductive elements disposed on said reference surface, each said element forming a first, capacitor electrode and the corresponding corneal surface forming the other capacitor electrode, and said means for determining said distance is a capacitance measurement system adapted to determine said distance data based on the capacitance of said capacitors.

17. The system of claim 1 wherein said means for determining said distance data are acoustic means.

18. The system of claim 1 wherein said means for determining said distance data are opto-acoustical means.

19. The system of claim 1 wherein said reference member further comprises an array of acoustic transducers disposed on said reference surface and adapted to generate and detect acoustic waves across said distance, and said means for determining said distance data is an acoustic measurement system adapted to determine said distance data based on the frequency of said acoustic waves.

20. The system of claim 1 wherein said reference member is adapted to form with said surface of said eye an acoustic chamber including an acoustic microphone, and said means for determining said distance data is an opto-acoustic measurement system comprising a light source emitting a light beam of a wavelength selected for absorption by a constituent within said chamber, a modulator adapted to modulate said light beam at a frequency selected to excite acoustic waves by absorption of said modulated radiation in said chamber, said acoustic microphone adapted to detect said acoustic waves across said distance, and means for determining said distance data based on the frequency of said acoustic waves.

21. A system for determining information concerning the topography of a portion of the exterior surface of the eye, the system comprising:

a member having a rigid surface of a predetermined shape for overlying said portion of the eye, said rigid surface of predetermined shapes, said reference surface being positionable in close proximity to and directed toward the exterior surface of the eye, a light source for introducing radiation to said exterior surface of the eye while said rigid reference member is positioned adjacent to said surface of the eye, said radiation passing through said rigid mender, a light detector for detecting the radiation, returning through said rigid member, reflected from a multiplicity of points over the area of said eye surface sufficient to represent the topography of the surface of the eye, light refracting means, associated with said rigid member, for substantially directing and returning radiation to the direction of said incoming radiation, and means for determining the topography of said surface of the eye from said introduced radiation and said detected radiation.

22. The system of claim 21 wherein said means for determining topography comprises a deflectometry-based system.

23. The system of claim 21 wherein said means for determining topography comprises a rasterography-based system.

24. The system of claim 21 wherein said means for determining topography comprises a Moire deflectometry-based system.

25. A method for determining information concerning the topography of a portion of the exterior surface of the eye comprising the steps of:

(a) providing a rigid reference member having a reference surface of a predetermined shape; said reference surface lying over said portion of the eye and being directed toward the exterior surface of the eye, (b) holding said rigid reference member stationary to the surface of the eye in the manner that there is a distance between the examined exterior surface of the eye and said reference surface of said reference member, (c) determining distance data over a multiplicity of data points sufficient in number and spacing to represent the local topography of said surface of the eye, and (d) determining the desired information concerning the topography of said surface of the eye from said distance data in reference to said predetermined shape of said reference surface.

26. The method of claim 25 wherein reference member is transparent to selected radiation and said step of determining said distance data is performed using an optical technique.

27. The method of claim 26 wherein said optical technique is white light interferometry.

28. The method of claim 26 wherein said optical technique is single color interferometry.

29. The method of claim 26 wherein said optical technique is laser radar ranging.

30. The method of claim 25 wherein said reference member further comprises an array of conductive elements disposed on said reference surface each forming a first capacitor electrode and the corresponding corneal surface forming the another capacitor electrode and said step of determining said distance data is performed using an capacitance technique adapted to determine said distance data based on the capacitance of said capacitors.

31. The method of claim 25 wherein said step of determining said distance data is performed using an acoustic technique.

32. The method of claim 25 wherein said step of determining said distance data is performed using an opto-acoustical technique.

33. The method of claim 25 wherein said reference member further comprises an array of acoustic transducers disposed on said reference surface said step of determining said distance data comprises the steps of:

(e) generating acoustic waves of different frequencies across said distance for each acoustic transducer, (f) detecting an acoustic wave having a resonance frequency, (g) determining a distance between said acoustic transducer and said exterior surface of the eye based on the resonance frequency of said acoustic wave, and (h) repeating steps (e), (f) and (g) for said individual transducers to determine said distance data.

34. The method of claim 25 wherein said reference member is adapted to form with said surface of the eye an acoustic chamber including an acoustic microphone, and said step of determining said distance data comprises the steps of:

(e) generating a light beam of a wavelength selected for absorption by a constituent within said chamber at a selected location, (f) modulating said light beam at a frequency selected to excite acoustic waves by absorption of said modulated radiation in said chamber, (g) detect said acoustic waves across said distance, (h) determining said distance, at said selected location, based on the frequency of said acoustic waves, and (i) repeating steps (e), (f), (g) and (h) at another selected location to determine said distance data over a multiplicity of data points sufficient in number and spacing to represent the desired information concerning the topography of the surface of the eye.

35. The method of claim 25 wherein reference member is transparent to selected optical radiation and said steps (c) and (d) include:

irradiating through said reference member the corneal surface of the eye, detecting altered light signal that is dependent upon a distance between said corneal surface of the eye and said reference surface, said detecting step including scanning an x,y area of said reference member and collecting said altered light signal with an x,y resolution on the order of about 50 μm, digitizing said altered light signal of said portion of interest of the corneal surface, determining from said digitized signal distance data between said out-of-contact reference surface and said portion of the corneal surface of the eye over a multiplicity of x,y data points sufficient in number and spacing to represent the local topography of the surface of the eye relative to said reference surface, and determining the desired information concerning the topography of said portion of the corneal surface of the eye from said distance data corresponding to said x,y data points in reference to said predetermined shape of said reference surface.

36. The method of claim 35 wherein said reference surface is concave and substantially spherical to approximate the corneal surface of the eye to attain small distance between said rigid reference surface and said corneal surface over said portion of the eye, enabling small differences in topography of the eye surface to be detected as relatively large percentage changes in the distance data.

37. The method of claim 35 or 36 wherein said step of determining the desired information concerning the topography of said corneal surface further comprising fitting said distance data to a polynomial, said polynomial containing low order terms representing translational displacements, offset, and angular tilting of said rigid reference surface relative to said corneal surface, said polynomial also containing higher-order terms representing information about the topography of the cornea.

38. A method for determining information concerning the topography of a portion of the exterior surface of the eye comprising the steps of:

(a) providing a rigid member having an outside surface and a inside surface of predetermined shapes, said inside surface being directed toward the exterior surface of the eye and overlying said portion of the eye, (b) holding said rigid member stationary to the surface of the eye, (c) introducing light, passing through said rigid member, to said exterior surface of the eye, (d) detecting radiation, returning through said rigid member, reflected from a multiplicity of points over the area of said eye surface sufficient to represent the topography of the surface of the eye, (e) determining the desired information concerning the topography of said exterior surface of the eye from said introduced and reflected radiation.

39. The method of claim 38 wherein said determining step is performed using a deflectometry-based technique.

40. The method of claim 38 wherein said determining step is performed using a rasterography-based technique.

41. The method of claim 38 wherein said determining step is performed using a Moire deflectometry-based technique.

* * * * *